(12) United States Patent
Bevirt et al.

(10) Patent No.: US 6,705,871 B1
(45) Date of Patent: *Mar. 16, 2004

(54) METHOD AND APPARATUS FOR PROVIDING AN INTERFACE MECHANISM FOR A COMPUTER SIMULATION

(75) Inventors: JoeBen Bevirt, Palo Alto; David F. Moore, Redwood City; John Q. Norwood, San Francisco; Louis B. Rosenberg, Pleasanton; Mike D. Levin, Sunnyvale, all of CA (US)

(73) Assignee: Immersion Corporation, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/448,536

(22) Filed: Nov. 22, 1999

Related U.S. Application Data

(63) Continuation of application No. 08/709,012, filed on Sep. 6, 1996, now Pat. No. 6,024,576.

(51) Int. Cl.[7] ............................ G09B 23/28; G09G 5/00
(52) U.S. Cl. ........................................ 434/262; 345/156
(58) Field of Search ................................ 434/262, 267; 345/156, 158, 161, 184; 414/5

(56) References Cited

U.S. PATENT DOCUMENTS

| | | |
|---|---|---|
| 2,906,179 A | 9/1959 | Bower ........................ 90/13.5 |
| 3,157,853 A | 11/1964 | Hirsch |
| 3,220,121 A | 11/1965 | Cutler |

(List continued on next page.)

FOREIGN PATENT DOCUMENTS

| | | | |
|---|---|---|---|
| BV | 0 349 086 A1 | 1/1990 | |
| GB | 2 254 911 A | 10/1992 | |
| JP | 4-34610 | 2/1992 | |

(List continued on next page.)

OTHER PUBLICATIONS

Jacobsen, S.C. et al., "High Performance, High Dexterity, Force Reflective Teleoperator II," ANS Topical Meeting on Robotics & Remote Systems, Albuquerque, New Mexico Feb. 24–27, 1991, pp. 1–10.

Kotoku, Tetsuo et al., "Environment Modeling for the Interactive Display (EMID) Used in Telerobotic Systems," IEEE Nov. 3–5, 1991, pp. 99–1004.

Bejczy, Antal K., "The Phantom Robot: Predictive Displays for Teleoperation with Time Delay," IEEE 1990, pp. 546–550.

(List continued on next page.)

*Primary Examiner*—John Edmund Rovnak

(57) ABSTRACT

A mechanical interface for providing high bandwidth and low noise mechanical input and output for computer systems. A gimbal mechanism includes multiple members that are pivotably coupled to each other to provide two revolute degrees of freedom to a user manipulatable about a pivot point located remotely from the members at about an intersection of the axes of rotation of the members. A linear axis member, coupled to the user object, is coupled to at least one of the members, extends through the remote pivot point and is movable in the two rotary degrees of freedom and a third linear degree of freedom. Transducers associated with the provided degrees of freedom include sensors and actuators and provide an electromechanical interface between the object and a computer. Capstan band drive mechanisms transmit forces between the transducers and the object and include a capstan and flat bands, where the flat bands transmit motion and force between the capstan and interface members. Applications include simulations of medical procedures, e.g. epidural anesthesia, where the user object is a needle or other medical instrument, or other types of simulations or games.

43 Claims, 10 Drawing Sheets

U.S. PATENT DOCUMENTS

| | | |
|---|---|---|
| 3,490,059 A | 1/1970 | Paulsen et al. ............... 73/133 |
| 3,497,668 A | 2/1970 | Hirsch |
| 3,517,446 A | 6/1970 | Corlyson et al. |
| 3,623,064 A | 11/1971 | Kagan |
| 3,795,150 A | 3/1974 | Eckhardt ...................... 74/5.4 |
| 3,875,488 A | 4/1975 | Crocker et al. ............. 318/648 |
| 3,890,958 A | 6/1975 | Fister et al. ................ 128/2 S |
| 3,902,687 A | 9/1975 | Hightower |
| 3,903,614 A | 9/1975 | Diamond et al. |
| 3,911,416 A | 10/1975 | Feder |
| 3,919,691 A | 11/1975 | Noll ....................... 340/172.5 |
| 3,944,798 A | 3/1976 | Eaton ...................... 235/151.3 |
| 4,125,800 A | 11/1978 | Jones ......................... 318/681 |
| 4,148,014 A | 4/1979 | Burson ...................... 340/709 |
| 4,160,508 A | 7/1979 | Frosch et al. |
| 4,216,467 A | 8/1980 | Colston ................. 340/365 L |
| 4,236,325 A | 12/1980 | Hall et al. |
| 4,391,282 A | 7/1983 | Ando et al. ................. 128/660 |
| 4,398,889 A | 8/1983 | Lam et al. ..................... 434/45 |
| 4,436,188 A | 3/1984 | Jones ......................... 188/378 |
| 4,448,083 A | 5/1984 | Hayashi .................. 73/862.04 |
| 4,477,043 A | 10/1984 | Repperger ................. 244/223 |
| 4,513,235 A | 4/1985 | Acklam et al. |
| 4,550,617 A | 11/1985 | Fraignier et al. ........ 73/862.04 |
| 4,581,491 A | 4/1986 | Boothroyd |
| 4,599,070 A | 7/1986 | Hladky et al. |
| 4,604,016 A | 8/1986 | Joyce ............................ 414/7 |
| 4,632,341 A | 12/1986 | Repperger et al. .......... 244/230 |
| 4,638,798 A | 1/1987 | Shelden et al. ......... 128/303 B |
| 4,676,002 A | 6/1987 | Slocum ..................... 33/1 MP |
| 4,679,331 A | 7/1987 | Koontz ........................ 33/551 |
| 4,708,656 A | 11/1987 | de Vries et al. |
| 4,713,007 A | 12/1987 | Alban |
| 4,750,487 A | 6/1988 | Zanetti ................... 128/303 B |
| 4,769,763 A | 9/1988 | Trieb et al. .................. 364/559 |
| 4,775,289 A | 10/1988 | Kazerooni .................. 414/735 |
| 4,791,934 A | 12/1988 | Brunnett ..................... 128/653 |
| 4,794,392 A | 12/1988 | Selinko |
| 4,800,721 A | 1/1989 | Cemenska et al. ............ 60/393 |
| 4,803,413 A | 2/1989 | Kendig et al. .............. 318/648 |
| 4,811,608 A | 3/1989 | Hilton .................... 73/862.04 |
| 4,837,650 A * | 6/1989 | Kawada ..................... 360/267 |
| 4,879,556 A | 11/1989 | Duimel ........................ 341/20 |
| 4,888,877 A | 12/1989 | Enderle et al. ............... 33/559 |
| 4,891,764 A | 1/1990 | McIntosh |
| 4,896,554 A | 1/1990 | Culver .................. 74/471 XY |
| 4,907,970 A | 3/1990 | Meenen, Jr. ................. 434/45 |
| 4,907,973 A | 3/1990 | Hon ........................... 434/262 |
| 4,930,770 A | 6/1990 | Baker |
| 4,934,694 A | 6/1990 | McIntosh |
| 4,945,501 A | 7/1990 | Bell et al. .............. 364/571.05 |
| 4,961,038 A | 10/1990 | MacMinn ................... 318/696 |
| 4,961,138 A | 10/1990 | Gorniak ...................... 364/200 |
| 4,961,267 A | 10/1990 | Herzog ........................ 33/503 |
| 4,962,448 A | 10/1990 | DeMaio et al. ............. 364/146 |
| 4,982,504 A | 1/1991 | Soderberg et al. ............ 33/502 |
| 5,007,300 A | 4/1991 | Siva ....................... 74/471 XY |
| 5,019,761 A | 5/1991 | Kraft |
| 5,022,407 A | 6/1991 | Horch et al. |
| 5,035,242 A | 7/1991 | Franklin et al. |
| 5,038,089 A | 8/1991 | Szakaly |
| 5,040,306 A | 8/1991 | McMurtry et al. ............. 33/556 |
| 5,044,956 A | 9/1991 | Behensky et al. ............. 434/45 |
| 5,050,608 A | 9/1991 | Watanabe et al. ....... 128/653 R |
| 5,072,361 A | 12/1991 | Davis et al. ........... 364/167.01 |
| 5,078,152 A | 1/1992 | Bond et al. |
| 5,088,046 A | 2/1992 | McMurtry ............. 364/474.03 |
| 5,103,404 A | 4/1992 | McIntosh ............... 318/568.22 |
| 5,107,080 A | 4/1992 | Rosen ....................... 200/6 A |
| 5,116,051 A | 5/1992 | Moncrief et al. ........ 273/448 B |
| 5,126,948 A | 6/1992 | Mitchell et al. ........ 364/474.03 |
| 5,142,931 A | 9/1992 | Menahem .............. 74/471 XY |
| 5,143,505 A | 9/1992 | Burdea et al. .................. 414/5 |
| 5,148,377 A | 9/1992 | McDonald ................ 364/560 |
| 5,182,557 A | 1/1993 | Lang ............................ 341/20 |
| 5,184,306 A | 2/1993 | Erdman et al. ........ 364/474.05 |
| 5,184,319 A | 2/1993 | Kramer ....................... 364/806 |
| 5,185,561 A | 2/1993 | Good et al. .................. 318/432 |
| 5,186,629 A | 2/1993 | Rohen ......................... 434/114 |
| 5,193,963 A | 3/1993 | McAffee et al. ................ 414/5 |
| 5,209,131 A | 5/1993 | Baxter ....................... 73/865.8 |
| 5,212,473 A | 5/1993 | Louis |
| 5,220,260 A | 6/1993 | Schuler ........................ 318/561 |
| 5,223,776 A | 6/1993 | Radke et al. ............. 318/568.1 |
| 5,228,356 A | 7/1993 | Chuang ................. 74/471 XY |
| 5,230,623 A | 7/1993 | Guthrie et al. ................. 433/72 |
| 5,240,417 A | 8/1993 | Smithson et al. |
| 5,243,266 A | 9/1993 | Kasagami et al. ........ 318/568.1 |
| 5,251,127 A | 10/1993 | Raab ..................... 364/413.13 |
| 5,264,768 A | 11/1993 | Gregory et al. ............. 318/561 |
| 5,271,290 A | 12/1993 | Fischer |
| 5,275,174 A | 1/1994 | Cook |
| 5,275,565 A | 1/1994 | Moncrief ..................... 434/29 |
| 5,296,846 A | 3/1994 | Ledley ........................ 345/161 |
| 5,299,810 A | 4/1994 | Pierce et al. |
| 5,309,140 A | 5/1994 | Everett, Jr. et al. |
| 5,334,027 A | 8/1994 | Wherlock |
| 5,351,692 A | 10/1994 | Dow et al. ............. 128/662.06 |
| 5,379,663 A | 1/1995 | Hara ..................... 74/471 XY |
| 5,389,865 A | 2/1995 | Jacobus et al. ......... 318/568.11 |
| 5,396,266 A | 3/1995 | Brimhall ..................... 345/161 |
| 5,396,267 A | 3/1995 | Bouton ........................ 345/168 |
| 5,397,323 A | 3/1995 | Taylor et al. ................ 606/130 |
| 5,402,582 A | 4/1995 | Raab ........................... 33/503 |
| 5,405,152 A | 4/1995 | Katanics et al. ............. 273/438 |
| 5,412,880 A | 5/1995 | Raab ........................... 33/503 |
| 5,414,337 A | 5/1995 | Schuler ........................ 318/561 |
| 5,428,748 A | 6/1995 | Davidson et al. ........... 395/275 |
| 5,429,140 A | 7/1995 | Burdea et al. ............... 128/774 |
| 5,436,542 A | 7/1995 | Petelin et al. ................ 318/567 |
| 5,436,640 A | 7/1995 | Reeves ........................ 345/161 |
| 5,445,166 A | 8/1995 | Taylor ......................... 128/897 |
| 5,451,924 A | 9/1995 | Massimino et al. ....... 340/407.1 |
| 5,459,382 A | 10/1995 | Jacobus et al. ......... 318/568.11 |
| 5,466,213 A | 11/1995 | Hogan et al. |
| 5,482,051 A | 1/1996 | Reddy et al. ................ 128/733 |
| 5,491,477 A | 2/1996 | Clark et al. .................... 341/20 |
| 5,512,919 A | 4/1996 | Araki ........................ 345/156 |
| 5,513,100 A | 4/1996 | Parker et al. ........... 364/167.01 |
| 5,547,382 A | 8/1996 | Yamasaki et al. |
| 5,551,701 A | 9/1996 | Bouton et al. ................. 463/36 |
| 5,570,111 A | 10/1996 | Barrett et al. ................ 345/157 |
| 5,576,727 A | 11/1996 | Rosenberg et al. ......... 345/179 |
| 5,587,937 A | 12/1996 | Massie et al. ............... 364/578 |
| 5,589,828 A | 12/1996 | Armstrong ................... 341/20 |
| 5,589,854 A | 12/1996 | Tsai ............................ 345/161 |
| 5,591,924 A | 1/1997 | Hilton ................... 73/862.043 |
| 5,623,582 A | 4/1997 | Rosenberg ..................... 395/99 |
| 5,625,576 A | 4/1997 | Masie et al. ................. 364/578 |
| 5,629,594 A | 5/1997 | Jacobus et al. ......... 318/568.11 |
| 5,642,469 A | 6/1997 | Hannaford et al. ........... 395/99 |
| 5,643,087 A | 7/1997 | Marcus et al. ................. 463/38 |
| 5,656,901 A | 8/1997 | Kurita ........................ 318/436 |
| 5,666,138 A | 9/1997 | Culver ........................ 345/161 |
| 5,666,473 A | 9/1997 | Wallace ...................... 345/420 |
| 5,691,898 A | 11/1997 | Rosenberg et al. ......... 364/190 |
| 5,694,013 A | 12/1997 | Stewart et al. .............. 318/561 |
| 5,721,566 A | 2/1998 | Rosenberg et al. ......... 345/161 |
| 5,731,804 A * | 3/1998 | Rosenberg .................. 345/156 |
| 5,734,373 A | 3/1998 | Rosenberg .................. 345/161 |
| 5,739,811 A | 4/1998 | Rosenberg et al. ......... 345/161 |

| | | |
|---|---|---|
| 5,742,278 A | 4/1998 | Chen et al. ................ 345/156 |
| 5,755,577 A | 5/1998 | Gillio ........................ 434/262 |
| 5,766,016 A | 6/1998 | Sinclair et al. |
| 5,767,839 A | 6/1998 | Rosenberg ................. 345/161 |
| 5,769,640 A | 6/1998 | Jacobus et al. ............. 434/262 |
| 5,785,630 A | 7/1998 | Bobick et al. |
| 5,790,108 A | 8/1998 | Salcudean et al. ......... 345/184 |
| 5,805,140 A | 9/1998 | Rosenberg et al. ......... 345/161 |
| 5,816,105 A | 10/1998 | Adelstein ............... 74/471 XY |
| 5,821,920 A | 10/1998 | Rosenberg et al. ......... 345/156 |
| 5,828,197 A | 10/1998 | Martin et al. ............... 318/567 |
| 6,020,875 A | 2/2000 | Moore et al. ............... 345/156 |
| 6,024,576 A * | 2/2000 | Bevirt et al. ................ 434/262 |
| 6,104,382 A | 8/2000 | Martin et al. ............... 345/161 |
| 6,193,519 B1 * | 2/2001 | Eggert et al. ............... 434/262 |
| 6,246,390 B1 | 6/2001 | Rosenberg |
| 6,323,837 B1 | 11/2001 | Rosenberg |

FOREIGN PATENT DOCUMENTS

| | | |
|---|---|---|
| WO | WO94/00052 | 1/1994 |
| WO | WO94/26167 | 11/1994 |
| WO | WO95/02233 | 1/1995 |
| WO | WO95/02801 | 1/1995 |
| WO | WO95/10080 | 4/1995 |
| WO | WO95/20787 | 8/1995 |
| WO | WO95/32459 | 11/1995 |
| WO | WO96/16397 | 5/1996 |
| WO | WO96/22591 | 7/1996 |
| WO | WO96/39944 | 12/1996 |
| WO | WO95/20788 | 8/1997 |

OTHER PUBLICATIONS

Kilpatrick, Paul, "The Use of a Kinesthetic Supplement in an Interactive Graphics System", Univ. of North Carolina at Chapel Hill, 1976, pp. 1–175.

Ramstein, Christophe, "Combining Haptic and Braille Technologies: Design Issues and Pilot Study", ASSETS '96, 2$^{nd}$ Annual ACM Conf. on Assistive Technologies, ACM SIGRAPH, Apr. 1996, pp. 37–44.

Iwata, Hiroo, "Artificial Reality with Force–feedback: Development of Desktop Virtual Space with Compact Master Manipulator", Computer Grahics, vol. 24, No. 4, Aug. 1990, pp. 165–170.

Payette et al., "Evaluation of a Force Feedback (Haptic) Computer Pointing Device in Zero Gravity", DSC–vol. 58, Proceedings of the ASME Dynamics Systems and Control Division, ASME 1996, pp. 547–553.

Hirota, Koichi, "Development of Surface Display," IEEE 0–7803–1363, 1993, pp. 256–262.

Bostrom, M. et al., "Design of An Interactive Lumbar Puncture Simulator With Tactile Feedback," IEEE 0–7803–1363, 1993, pp. 280–286.

Yokohoji, Y. et al., "What you Can See is What You Can Feel—Development of a Visual/Haptic Interface to Virtual Environment," Proceedings of VRAIS '96, IEEE 1996, pp. 46–54.

Ramstein, Christophe, "The Pantograph: A Large Workspace Haptic Device for a Multimodal Human–Computer Interaction", Computer–Human Interaction, CHI 1994.

Millman, P. et al., "Design of a Four Degree–of–Freedom Force–Reflecting Manipulandum with a Specified Force/Torque Workspace," Proc. of 1991 IEEE Int'l Conf. on Robotics and Automation, IEEE CH2969–4, 1991, pp. 1488–1493.

Hayward, V. et al., "Design and Multi–Objective Optimization of a Linkage for a Haptic Interface," Advances in Robot Kinematics and Computationed Geometry, 1994, pp 359–368.

Stone, R. et al., "Virtual Environment Training Systems for Laparoscopic Surgery," The Journal of Medicine and Virtual Reality, 1995, pp. 42–51.

Buttolo, Pietro et al., "Pen–Based Force Display for Precision Manipulation in Virtual Environments," IEEE Mar. 1995, pp. 1–8.

Tan, Hong Z. et al., "Human Factors for the Design of Force–Reflecting Haptic Interfaces," Tan, Srinivasan, Eberman, & Chang, ASME WAM 1994, pp. 1–11.

Ellis, R.E. et al., "Design and Evaluation of a High–Performance Prototype Planar Haptic Interface," ASME Dec. 3, 1993, DSC–vol. 49, pp. 55–64.

Adelstein Bernard D. et al., "A High Performance Two Degree–of–Freedom Kinesthetic Interface," Massachusetts Institute of Technology 1992, pp. 108–112.

Colgate J. Edward et al., Implementation of Stiff Virtual Walls in Force–Reflecting Interfaces, Sep. 22, 1993.

Iwata, Hiroo et al, Volume Haptization, IEEE 1993, pp. 16–18.

Fischer, Patrick et al., "Specification and Design of Input Devices for Teleoperation," 1990.

Burdea, Grigore et al., "Distributed Virtual Force Feedback," IEEE, May 2, 1993, pp. 25–44.

Rosenberg, Louis B., "The Use of Virtual Fixtures as Perceptual Overlays to Enhance Operator Performance in Remote Environments," Air Force Material Command, Sep. 1992, pp. 1–42.

Rosenberg, Louis B., The Use of Virtual Fixtures to Enhance Operator Performance in Time Delayed Teleoperation, Armstrong Laboratory, Mar. 1993, pp. 1–45.

Rosenberg, Louis B., "Perceptual Design of a Virtual Rigid Surface Contact," Center for Design Reseach Stanford University, Air Force Material Command, Apr. 1993, pp. 1–41.

Rosenberg, Louis B. et al., "Perceptual Decomposition of Virtual Haptic Surfaces," IEEE, Oct. 1993.

Rosenberg, Louis B. et al., "Virtual Fixtures as Tools to Enhance Operator Performance in Telepresence Environments," SPIE Telemanipulator Technology, 1993.

Rosenberg, Louis B., "Virtual Haptic Overlays Enhance Performance in Telepresence Tasks," SPIE 1994.

Burdea, Grigore et al., "Dextrous Telerobitcs with Force Feedback–An Overview," Robotica 1991, vol. 9.

Yamakita, M. et al., Tele–Virtual Reality of Dynamic Mechanical Model, IEEE Jul. 7–10, 1992, pp. 1103–1110.

Adlestein, Bernard D. et al., "Design and Implementation of a Force Reflecting Manipulandum for Manual Control Research," 1992, pp. 1–24.

Ouh–young, Ming et al., "Force Display Performs Better than Visual Display in a Simple 6–D Docking Task," IEEE 1989, pp. 1462–1466.

Hannaford, Blake et al., "Performance Evaluation of a Six–Axis Generalized Force–Reflecting Teleoperator," IEEE May/Jun. 1991, vol. 21, No. 3, pp. 620–633.

Kim, Won S. et al., A Teleoperation Training Simulator with Visual and Kinesthetic Force Virtual Reality.

Burdea, Grigore et al., "A Portable Dextrous Master with Force Feedback," Presence: Teleoperators and Virtual Environments, MIT Press, Jun. 1991.

Fisher, S.S. et al., "Virtual Environment Display System," ACM Interactive 3D Graphics, Oct., 1986.

3D Human Interface Tool, Immersion Probe™, Immersion Human Interface Corporation 1994.

Meyer, Kenneth et al., "A Survey of Position Trackers," The Massachusetts Institute of Technology 1992, Presence, vol. 1, No. 2.

Smith, Geoffrey, "Call It Palpable Progress," Business Week, Oct. 9, 1995, pp. 93, 96.

Minsky, Margaret et al., "Feeling and Seeing: Issues in Force Display," ACM 1990, pp. 235–242.

Herndon, J.N. et al., "The State–of–the–Art Model M–2 Maintenance System," Proceedings of the 1984 National Topical Meeting on Robotics and Remote Handling in Hostile Environments, American Nuclear Society, pp. 59–65.

Batter, James J. et al., "Grope–1: A Computer Display to the Sense of Feel," pp. TA–4–188–TA–4–192.

Gotow, J.K., et al., "Perception of Mechanical Properties at the Man–Machine Interface," IEEE 1987, pp. 688–689.

Atkinson, William D. et al, "Computing with Feeling," Comput. & Graphics, vol. 2, No. 2–E, pp. 97–103.

Noll, A. Michael, "Man–Machine Tactile Communication Dissertation," Polytechnic Institute of Brooklyn, Jun. 1971, pp. 1–88.

Ouh–Young, Ming, "Force Display in Molecular Docking," Chapel Hill 1990, pp. 1–85.

Ouh–young, Ming et al., "Using a Manipulator for Force Display in Molecular Docking," IEEE 1988, pp. 1824–1829.

Wiker, Steven F. et al., "Development of Tactile Mice for Blind Access to Computers: Importance of Stimulation Locus, Object Size, and Vibrotactile Display Resolution," Proceedings of the Human Factors Society 35th Annual Meeting 1991, pp. 708–712.

Tavkhelidze, D.S. "Kinematic Analysis of Five–Link Spherical Mechanisms," Mechanism and Machine Theory 1974, vol. 9, pp. 181–190.

Adachi, Yoshitaka et al., "Sensory Evaluation of Virtual Haptic Push–Buttons," Technical Research Center, Suzuki Motor Corporation, Nov. 1994.

Tan, Hong Z et al., "Manual Resolution of Compliance When Work and Force Cues are Minimized," ASME 1993, DSC–vol. 49, pp. 99–104.

Iwata, Hiroo, "Pen–based Haptic Virtual Environment," Institute of Engineering Mechanics, University of Tsukuba, Japan, pp. 287–292.

Kotoku, Tetsuo, "A Predictive Display with Force Feedback and its Application to Remote Manipulation System with Transmission Time Display," IEEE 1992, Jul. 7–10, 1992, pp. 239–246.

Howe, Robert D., "Task Performance with a Dextrous Teleoperated Hand System," Proceedings of SPIE, Nov. 1992, vol. 1833, pp. 1–9.

Snow, E. et al., "Compact Force–Reflecting Hand Controller," JPL, Apr. 1991, vol. 15, No. 3, Item No. 153, pp. 1–15a.

McAffee, Douglas A., "Teleoperator System/Telerobot Demonstrator: Force Reflecting Hand Controller Equipment Manual," JPL Jan. 1988, pp. 3–8, 11, and A–34.

Schmult, Brian et al., "Application Areas for a Force–Feedback Joystick," ASME 1993, DSC–vol. 49, pp. 47–54.

Hasser, Christopher John, "Tactile Feedback for a Force–Reflecting Haptic Display," The School of Engineering, University of Dayton, Dec. 1995, pp. iii–xii & 1–96.

Russo, Massimo Andrea, "The Design and Implementation of a Three Degree–of–Freedom Force Output Joystick," Department of Mechanical Engineering, May 11, 1990, pp. 9–40 & 96 & 97.

Rosenberg, L.B., "Commercially Viable Force Feedback Controller for Individuals with Neuromotor disabilities," United States Air Force Armstrona Laboratory, May, 1996.

Rosenberg, Louis, Ph.D., "Using Force Feeback to Enhance Human performance in Graphical User Interfaces," 4/96.

Repperger, D.W., "Active Force Reflection Devices in Teleoperation," IEEE Control Systems.

Winey, III, Calvin McCoy, "Computer Simulated visual and Tactile Feedback as an Aid to Manipulator and Vehicle Control," Master of Science in Mechanical Engineering, Massachusetts Institute of technology, 1981.

Baigrie, "Electric Control Loading –A Low Cost, High Performance Alternative," *Proceedings of Interservice/Industry Training Systems Conference*, pp. 247–254, Nov. 6–8, 1990.

Iwata, "Pen–based Haptic Virtual Environment," 0–7803–1363–Jan. 1993 IEEE, pp. 287–292, 1993.

Russo, "The Design and Implementation of a Three Degree of Freedom Force Output Joystick," *MIT Libraries Archives* pp. 1–131, May 1990, archived Aug. 14, 1990.

Brooks et al., "Hand Controllers for Teleoperation –A State–of–the–Art Technology Survey and Evaluation," *JPL Publication* 85–11, NASA–CR–175890; N85–28559, pp. 1–84, Mar. 1, 1985.

Jones et al., "A perceptual analysis of stiffness," ISSN 0014–4819 Springer International (Springer–Verlag); *Experimental Brain Research*, vol. 79, No. 1, pp. 150–156, 1990.

Burdea et al., "Distributed Virtual Force Feedback, Lecture Notes for Workshop on Force Display in Virtual Environments and its Application to Robotic Teleoperation," 1993 *IEEE International Conference on Robotics and Automation*, pp. 25–44, May 2, 1993.

Snow et al., Model–X–Force–Reflecting–Hand–Controller, NT Control No. NPO–17851; JPL Case No. 7348, pp. 1–4 with 45 pages of attachments, Jun. 15, 1989.

Ouh–Young, "Force Display in Molecular Docking," Doctoral Dissertation, University of North Carolina at Chapel Hill, UMI Order No. 9034744, pp. 1–369, 1990.

Tadros, "Control System Design for a Three Degree of Freedom Virtual Environment Simulator Using Motor/Brake Pair Actuators," *MIT Archive*, pp. 1–88, Feb. 1990, archived Aug. 13, 1990.

Caldwell et al., "Enhanced Tactile Feedback (Tele–Taction) Using a Multi–Functional Sensory System," 1050–4729/93, pp. 955–960, 1993.

Adelstein et al., "Design and Implementation of a Force Reflecting Manipulandum for Manual Control research," DSC–vol. 42, *Advances in Robotics*, pp. 1–12, 1992.

Gotow et al., "Controlled Impedance Test Apparatus for Studying Human Interpretation of Kinesthetic Feedback," WA11–11:00, pp. 332–337.

Stanley et al., "Computer Simulation of Interacting Dynamic Mechanical Systems Using Distributed Memory Parallel Processors," DSC–vol. 42, *Advances in Robotics*, pp. 55–61, ASME 1992.

Russo, "Controlling Dissipative Magnetic Particle Brakes in Force Reflective Devices," DSC–vol. 42, *Advances in Robotics*, pp. 63–70, ASME 1992.

Kontarinis et al., "Display of High–Frequency Tactile Information to Teleoperators," *Telemanipulator Technology and Space Telerobotics*, Won S. Kim, Editor, Proc. SPIE vol. 2057, pp. 40–50, Sep. 7–9, 1993.

Patrick et al., "Design and Testing of A Non–reactive, Fingertip, Tactile Display for Interaction with Remote Environments," *Cooperative Intelligent Robotics in Space*, Rui J. deFigueiredo et al, Editor, Proc. SPIE vol. 1387, pp. 215–222, 1990.

Adelstein, "A Virtual Environmen System For The Study of Human Arm Tremor," *Ph.D. Dissertation*, Dept. of Mechanical Engineering, MIT, Jun. 1989, archived Mar. 13, 1990.

Bejczy, "Sensors, Controls, and Man–Machine Interface for Advanced Teleoperation," *Science*, vol. 208, No. 4450, pp. 1327–1335, 1980.

Bejczy et al., "Generalization of Bilateral Force–Relating Control of Manipulators," *Proceedings Of Fourth CISM–IFToMM*, Sep. 8–12, 1981.

McAffee et al., "Teleoperator Subsystem/Telerobot Demonstrator: Force Reflecting Hand Controller Equipment Manual," *JPL* 1988, JPL D–5172.

Minsky, "Computational Haptics: The Sandpaper System for Synthesizing Texture for a Force–Feedback Display," *Ph.D. Dissertation*, MIT, Jun. 1995, archived Jul. 6, 1995.

Jacobsen et al., "High Performance, Dextrous Telerobotic Manipulator With Force Reflection," *Intervention/ROV '91 Conference & Exposition*, Hollywood, Florida, May 21–23, 1991.

Shimoga, "Finger Force and Touch Feedback Issues in Dexterous Telemanipulation," *Proceedings of Fourth Annual Conference on Intelligent Robotic Systems for Space Exploration*, Rensselaer Polytechnic Institute, Sep. 30–Oct. 1, 1992.

IBM Technical Disclosure Bulletin, "Mouse Ball–Actuating Device With Force and Tactile Feedback," vol. 32, No. 9B, Feb. 1990.

Terry et al., "Tactile Feedback In A Computer Mouse," *Proceedings of Fourteenth Annual Northeast Bioengineering Conference, University of New Hampshire*, Mar. 10–11, 1988.

Howe, "A Force–Reflecting Teleoperated Hand System for the Study of Tactile Sensing in Precision Manipulation," *Proceedings of the 1992 IEEE International Conference on Robotics and Automation*, Nice, France, May 1992.

Eberhardt et al., "OMAR –A Haptic display for speech perception by deaf and deaf–blind individuals," *IEEE Virtual Reality Annual International Symposium*, Seattle, WA, Sep. 18–22, 1993.

Rabinowitz et al., "Multidimensional tactile display: Identification of vibratory intensity, frequency, and contractor area," *Journal of The Acoustical Society of America*, vol. 82, No. 4, Oct. 1987.

Bejczy et al., "Kinesthetic Coupling Between Operator and Remote Manipulator," *International Computer Technology Conference, The American Society of Mechanical Engineers*, San Francisco, CA, Aug. 12–15, 1980.

Bejczy et al., "A Laboratory Breadboard Systems For Dual–Arm Teleoperation," *SOAR '89 Workshop, JSC*, Houston, TX, Jul. 25–27, 1989.

Ouhyoung et al., "A Low–Cost Force Feedback Joystick and Its Use in PC Video Games," *IEEE Transactions on Consumer Electronics*, vol. 41, No. 3, Aug. 1995.

Marcus, "Touch Feedback in Surgery," *Proceedings of Virtual Reality and Medicine The Cutting Edge*, Sep. 8–11, 1994.

Bejczy, et al., "Universal Computer Control System (UCCS) For Space Telerobots," CH2413–3/87/0000/0318501.00 1987 IEEE, 1987.

* cited by examiner

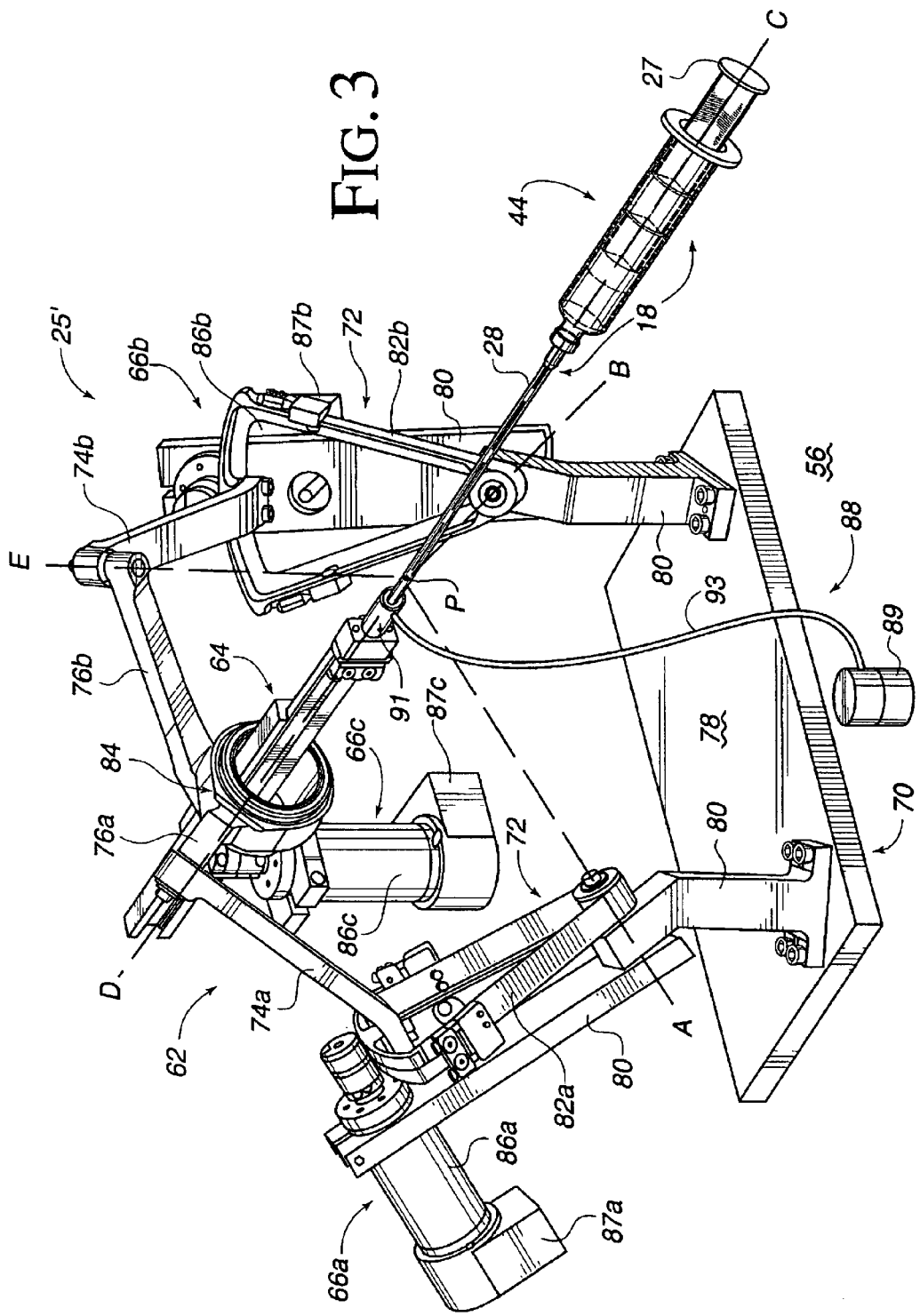

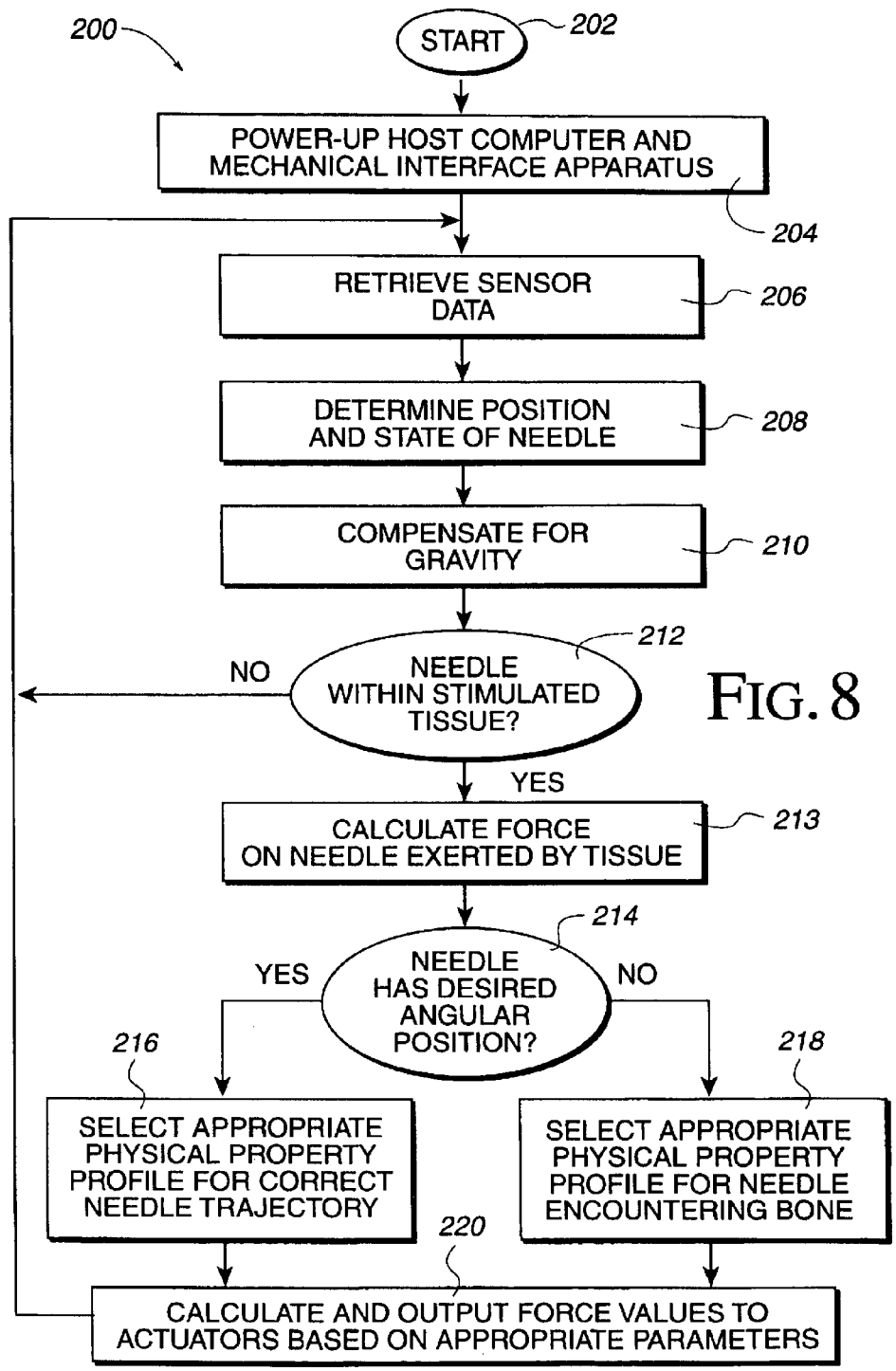

METHOD AND APPARATUS FOR PROVIDING AN INTERFACE MECHANISM FOR A COMPUTER SIMULATION

This is a Continuation application of prior application Ser. No. 08/709,012 filed on Sep. 6, 1996, now U.S. Pat. No. 6,024,576, the disclosure of which is incorporated herein by reference.

BACKGROUND OF THE INVENTION

The present invention relates generally to mechanical interface devices between humans and computers, and more particularly to mechanical devices for tracking manual manipulations and providing simulated force feedback.

Virtual reality computer systems provide users with the illusion that they are part of a "virtual" environment. A virtual reality system will typically include a computer processor, such as a personal computer or workstation, specialized virtual reality software, and virtual reality I/O devices such as display screens, head mounted displays, sensor gloves, etc. As virtual reality systems become more powerful and as the number of potential applications increases, there is a growing need for specific human/computer interface devices which allow users to interface with computer simulations with tools that realistically emulate the activities being represented within the virtual simulation.

One common use for virtual reality computer systems is for training. In many fields, such as aviation and vehicle and systems operation, virtual reality systems have been used successfully to allow a user to learn from and experience a realistic "virtual" environment. The appeal of using virtual reality computer systems for training relates, in part, to the ability of such systems to allow trainees the luxury of confidently operating in a highly realistic environment and making mistakes without "real world" consequences. One highly applicable field for the use of virtual training system is medical operations and procedures. A virtual reality computer system can allow a doctor-trainee or other human operator or user to "manipulate" a needle, scalpel or probe within a computer-simulated "body", and thereby perform medical procedures on a virtual patient. In this instance, the I/O device which is typically a 3D pointer, stylus, or the like is used to represent a surgical instrument such as a probe or scalpel. As the "probe" or "scalpel" moves within a provided space or structure, results of such movement are updated and displayed in a body image displayed on a screen of the computer system so that the operator can gain the experience of performing such a procedure without practicing on an actual human being or a cadaver.

Other uses for virtual reality computer systems include entertainment. Sophisticated simulations and video games allow a user to experience virtual environments with high degrees of realism, thus providing highly interactive and immersive experiences for the user.

For virtual reality systems to provide a realistic (and therefore effective) experience for the user, sensory feedback and manual interaction should be as natural and complete as possible. One essential sensory component for many experiences is the "haptic" and tactile senses. The haptic sense is typically related to the sense of touch not associated with tactility, such as the forces sensed when pushing or pulling on an object. The tactile sense is more concerned with the texture and feel of a surface or object. Medical operations and procedures using such medical instruments as catheters, laparoscopes, and needles have, a distinct haptic component that is essential to performing the procedures correctly and effectively. For example, epidural anesthesia is a highly delicate procedure performed by anesthesiologists in operations. In this procedure, a four inch needle is directed between two vertebrae in the lower back of the patient, through extremely dense tissue, and into an epidural space no larger than $\frac{1}{20}$th of an inch. Overshooting the epidural space may result in a "wet tap" puncturing the dura mater, resulting in severe spinal headaches for the patient, or, in extreme cases, damage to the spinal cord.

This insertion is accomplished only through the sense of feel, i.e., the haptic sense. The vast majority of physicians use a technique known as the "loss of resistance" method. The fluid in the syringe (typically a saline solution or simply air) is retarded by the dense ligaments as the needle is inserted. The administrator will feel a slight "pop" as the ligamentum flavum (the layer positioned just before the epidural space) is punctured, due to a slight pressure drop from entering the epidural space. The contents of the syringe then flow freely into the epidural space, gently expanding the separation of the two tissue layers. A catheter can subsequently be fed through the center of the epidural needle so that an anesthetic can be metered through an IV.

Currently there is no practical and effective training tool to assist trainees in developing proficiency in the administration of epidural anesthesia and like medical procedures. Mannequins and cadavers often do not meet many of the needs of trainees for such precise manipulations. Thus, a highly accurate virtual reality system would be ideal for this and other types of applications, especially a "high bandwidth" interface system, which is an interface that accurately responds to electronic signals having fast changes and a broad range of frequencies as well as mechanically transmitting such signals accurately to a user.

There are number of devices that are commercially available for interfacing a human with a computer for virtual reality simulations. Some of these devices provide "force feedback" to a user, i.e., the user interface device outputs forces through the use of computer-controlled actuators and sensors to allow the user to experience haptic sensations. However, none of these devices is tailored for such precise operations as epidural anesthesia. For example, in typical multi-degree of freedom apparatuses that include force feedback, there are several disadvantages. Since actuators which supply realistic force feedback tend to be large and heavy, they often provide inertial constraints. There is also the problem of coupled actuators. In a typical force feedback device, a serial chain of links and actuators is implemented to achieve multiple degrees of freedom for a desired object positioned at the end of, the chain, i.e., each actuator is coupled to the previous actuator. The user who manipulates the object must carry the inertia of all of the subsequent actuators and links except for the first actuator in the chain, which is grounded. While it is possible to ground all of the actuators in a serial chain by using a complex transmission of cables or belts, the end result is a low stiffness, high friction, high damping transmission which corrupts the bandwidth of the system, providing the user with an unresponsive, and inaccurate interface. These types of interfaces also introduce tactile "noise" to the user through friction and compliance in signal transmission and limit the degree of sensitivity conveyed to the user through the actuators of the device.

Other existing devices provide force feedback to a user through the use of a glove or "exoskeleton" which is worn over the user's appendages, such as fingers, arms, or body. However, these systems are not easily applicable to simulation environments such as those needed for medical procedures or simulations of vehicles and the like, since the forces applied to the user are with reference to the body of the user, not to a manipulated instrument or control, and the absolute location of the user's appendages or a manipulated instrument are not easily calculated. Furthermore, these devices tend to be complex mechanisms in which many actuators must be used to provide force feedback to the user.

In addition, existing force feedback devices are typically bulky and require that at least a portion of the force feedback mechanism extend into the workspace of the manipulated medical instrument. For example, in simulated medical procedures, a portion of the mechanism typically extends past the point where the skin surface of the virtual patient is to be simulated and into the workspace of the manipulated instrument. This can cause natural actions during the medical procedure, such as placing one's free hand on the skin surface when inserting a needle, to be strained, awkward, or impossible and thus reduces the realism of the simulation. In addition, the mechanism intrudes into the workspace of the instrument, reducing the workspace of the instrument and the effectiveness and realism of many force feedback simulations and video games. Furthermore, this undesired extension into the workspace often does not allow the force feedback mechanism to be easily housed in a protective casing and concealed from the user.

Furthermore, prior force feedback devices often employ low fidelity actuation transmission systems, such as gear drives. For higher fidelity, cable drive systems may be used. However, these systems require that a drive capstan be wrapped several times with a cable and that the cable be accurately tensioned, resulting in considerable assembly time of the force feedback device. There is also energy loss associated with the cable deflection as the capstan turns.

Therefore, a high fidelity human/computer interface tool which can provide force feedback in a constrained space to a manipulated object remote from the mechanism, and which can provide high bandwidth, accurate forces, is desirable for certain applications.

SUMMARY OF THE INVENTION

The present invention provides a mechanical interface apparatus and method which can provide highly realistic motion and force feedback to a user of the apparatus. The preferred apparatus includes a gimbal mechanism which provides degrees of freedom to a user manipulatable object about a remote pivot point such that the gimbal mechanism is entirely within a single hemisphere of a spherical workspace of the user object. In addition, a band drive mechanism provides mechanical advantage in applying force feedback to the user, smooth motion, and reduction of friction, compliance, and backlash of the system. The present invention is particularly well suited to simulations of medical procedures using specialized tools, as well as simulations of other activities, video games, etc.

Specifically, a mechanism of the present invention includes a gimbal mechanism for providing motion in two degrees of freedom. The gimal mechanism includes multiple members that are pivotably coupled to each other to provide two revolute degrees of freedom about a pivot point located remotely from the members. The pivot point is located at about an intersection of the axes of rotation of the members. A linear axis member is coupled to at least one of the members, extends through the pivot point and is movable in the two revolute degrees of freedom. The linear axis member preferably is or includes a user manipulatable object.

In a preferred embodiment, the gimbal mechanism includes five members forming a closed loop chain such that each of the five members is pivotably coupled to two other members of said five members. The multiple members of the gimbal mechanism are positioned exclusively within a hemisphere of a sphere defined by the workspace provided by the gimbal mechanism, i.e., on one side of a plane intersecting the remote pivot point, where the pivot point is at a center of the sphere. Preferably, the user manipulatable object is independently translatable with respect to the gimbal mechanism along a linear axis in a third degree of freedom through the pivot point, and at least a portion of the user object is positioned on the opposite side of the pivot point to the gimbal mechanism.

The gimbal mechanism interfaces the motion of the linear axis member in two degrees of freedom with a computer system. Transducers, including actuators and sensors, are coupled between members of the gimbal mechanism for an associated degree of freedom and are coupled to the computer system. The actuators provide a force on the linear axis member and the sensors sense the position of the linear axis member in the three degrees of freedom. Preferred user manipulatable objects include at least a portion of a medical instrument, such as a needle having a shaft and a syringe. A plunger actuator can be coupled to the needle for selectively providing a pressure to a plunger of the syringe and simulating ejected of a fluid through the needle. Alternatively, a spherical object or other type of object can be provided with the pivot point at about the object's center.

In another aspect of the present invention, the interface apparatus includes a band drive mechanism for transmitting forces from actuators to the user object and transmitting motion of the object to sensors. The band drive mechanism includes a capstan coupled to a rotating shaft of an actuator of the apparatus and to a member of the apparatus by a flat band. Force is applied to the member in at least one degree of freedom via the flat band when the shaft of the actuator is rotated. Preferably, a band drive mechanism is used for both rotary and linear degrees of freedom of the interface apparatus and transmits forces and motion with substantially no backlash. The flat band preferably includes two separate bands coupled between the capstan and the mechanism member.

In yet another aspect of the present invention, the interface apparatus is used in a computer simulation, such as a simulation of a medical procedure where the user-manipulable object is a medical instrument. The computer system determines the position of the user manipulatable object in at least one degree of freedom from sensors. A physical property profile is then selected. The profile includes a number of predetermined values, such as material stiffness, density, and texture, and the selection of the particular values of the profile is based on a position of the user object. Finally, a force on the user object is output based on a value in the selected profile using actuators coupled to the interface apparatus. Preferably, forces are also output from the actuators to compensate for the gravitational force resulting from the weight of the actuators and to allow the user object to be manipulated free from gravitational force. The profile is selected from multiple available profiles and is also dependent on a direction and trajectory of movement of the user object. In a described embodiment, the medical simulation is an epidural anesthesia simulation, and the user object includes a needle having a syringe. For example, one of the selected profiles can be to provide forces simulating the needle encountering a bone within tissue.

The interface apparatus of the present invention provides a unique gimbal mechanism having a remote pivot point that allows a user manipulatable object to be positioned on one side of the pivot point and the gimbal mechanism entirely on the other side of the pivot point. This provides a greater workspace for the user object and allows the mechanism to be protected and concealed. In other embodiments, the remote pivot point allows the user object to be rotated about the center of the object while advantageously allowing the user to completely grasp the object. Furthermore, the present invention includes easy-to-assemble band drive mechanisms that provide very low friction and backlash and high bandwidth forces to the user object, and are thus quite suitable for high precision simulations such as medical procedures. The structure of the apparatus permits transducers to be positioned such that their inertial contribution to the system is very low, thus enhancing the haptic response of the apparatus even further. Finally, a simulation process allows for realistic simulation of precise procedures such as epidural anesthesia. These advantages allow a computer system to have, more complete and realistic control over force feedback sensations experienced by a user of the apparatus.

These and other advantages of the present invention will become apparent to those skilled in the art upon a reading of the following specification of the invention and a study of the several figures of the drawing.

BRIEF DESCRIPTION OF THE DRAWINGS

FIG. 3 is a perspective view of a preferred embodiment of the mechanical apparatus of FIG. 2;

FIG. 8 a flow diagram illustrating a process of simulating an epidural anesthesia procedure using the mechanical apparatus of the present invention;

DETAILED DESCRIPTION OF PREFERRED EMBODIMENTS

Figure 1:
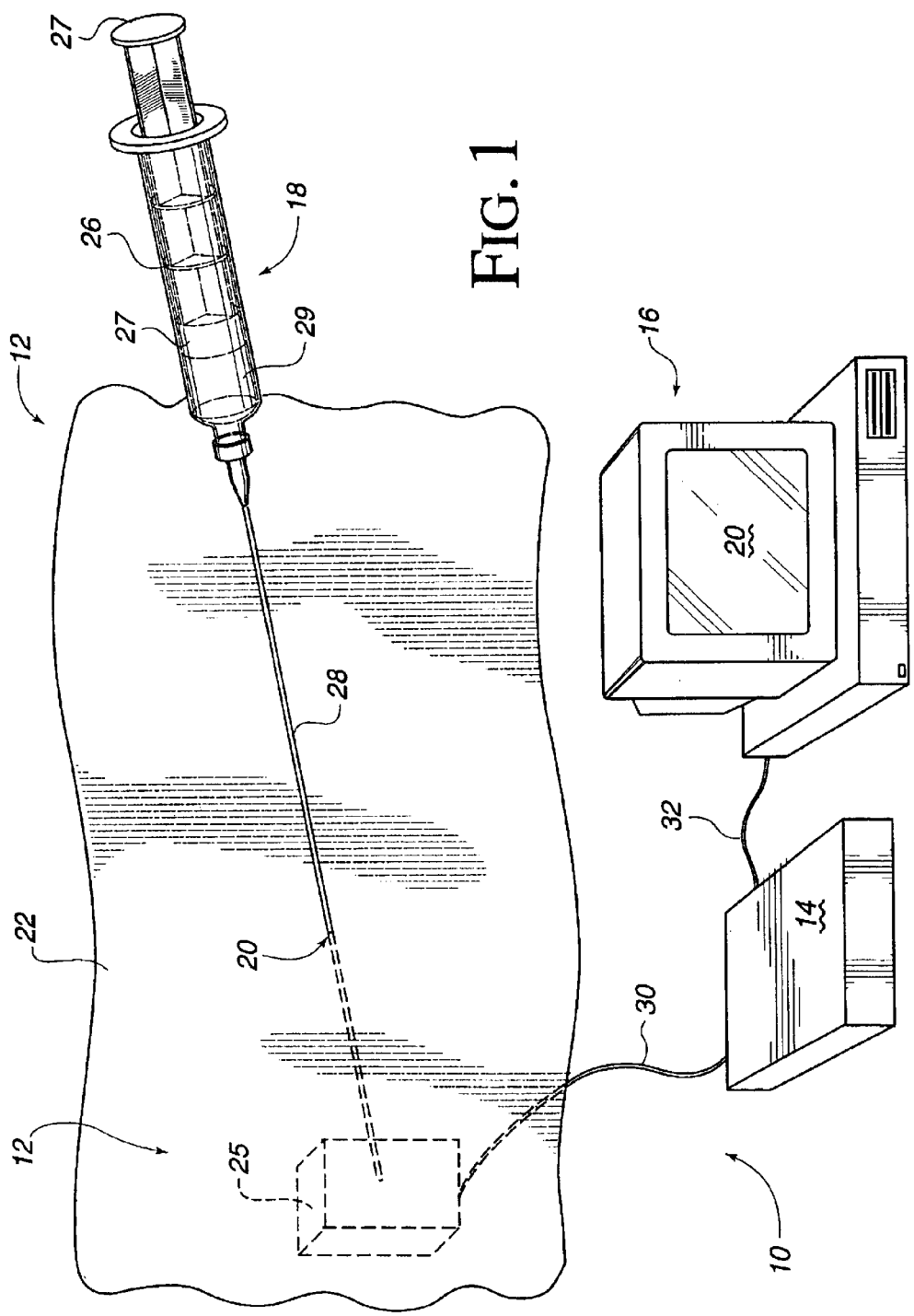
FIG. 1 is a perspective view of a virtual reality system which employs an apparatus of the present invention to interface a needle with a computer system in a medical simulation.

In FIG. 1, a virtual reality system 10 used to simulate a medical procedure includes a human/computer interface apparatus 12, an electronic interface 14, and a computer 16. The illustrated virtual reality system 10 is directed to a virtual reality simulation of a needle insertion procedure. An example of control software used in the simulation is provided in Appendix A. Suitable software drivers which interface such simulation software with computer input/output (I/O) devices are available from Immersion Human Interface Corporation of San Jose, Calif.

A needle/syringe tool (or "needle") 18 used in conjunction with one embodiment of the present invention is manipulated by an operator and, optionally, virtual reality images (and/or instructions or procedure information) may optionally be displayed on a screen 20 of the computer in response to such manipulations (or on a 3-D goggle display worn by the operator). Preferably, the computer 16 is a personal computer or workstation, such as an IBM-PC AT or Macintosh personal computer, or a SUN or Silicon Graphics workstation. Most commonly, the computer operates under the MS-DOS operating system in conformance with an IBM PC AT standard.

The needle 18 includes a syringe portion 26 and a shaft or needle portion 28. The syringe portion 26 is provided to hold a fluid and flow the fluid through the hollow shaft portion 28 when the operator moves plunger 27 through syringe housing 29. In one embodiment, the present invention is concerned with tracking the movement of the shaft portion 28 in three-dimensional space, where the shaft portion 28 has three (or more) free degrees of motion. Namely, the needle 18 can be preferably moved in a linear degree of freedom to simulate insertion of the needle in a patient, and can also preferably be rotated or pivoted in two degrees of freedom. This is a good simulation of the real use of a needle 18 in that a needle may be inserted and then removed, pivoted, and inserted again.

The human/interface apparatus 12 as exemplified herein is used to simulate a epidural anesthesia medical procedure. In such a procedure, an operator directs a needle between two vertebrae in the lower back of a patient, through extremely dense tissue, and into an epidural space no larger than 1/20th of an inch. Thus, in addition to the needle 18, the human/interface apparatus 12 may include a barrier 22 or other obstruction. The barrier 22 is used to represent a portion of the skin covering the body of a patient and is used to provide greater realism to the operator. For example, when inserting a needle 18 into a patient, it is natural for doctors to place the hand not handling the needle on the skin of the patient when inserting the needle to provide stability during the procedure. Barrier 22 allows trainees to simulate these types of natural actions. The shaft portion 28 is inserted into the "body" of the virtual patient at a point 20, which can simulate the area of the back covering the spine in an epidural anesthesia procedure, or other areas of a body in other medical procedures. Barrier 22 can be omitted from apparatus 12 in other embodiments.

A mechanical interface apparatus 25 for interfacing mechanical input and output is shown within the "body" of the patient in phantom lines. The shaft portion 28 extends to mechanical apparatus 25, which provides the mechanical support, degrees of freedom, and force simulation for needle 18 that realistically simulates an epidural anesthesia or other procedure. For example, the needle 18 can preferably move in a linear degree of freedom to simulate inserting the needle in the skin, and can also preferbly pivot such that the angular position of the needle with respect to the skin surface can be changed if the needle is inserted at an incorrect angle for a successful operation. In addition, mechanical apparatus 25 is preferably positioned entirely behind barrier 22 to allow the greatest realism in the simulation. Needle 18 or other instrument preferably can pivot about the insertion point 20, where the point 20 is not touching any physical mechanism of apparatus 25.

Furthermore, since the insertion and manipulation of the anesthesia needle is accomplished mainly through the sense of feel, the forces provided on tool 18 should be highly accurate and realistic to properly train anesthesiologists. For example, in epidural anesthesia procedures, the vast majority of physicians use a technique known as the "loss of resistance" method. The fluid in the syringe (typically a saline solution or air) is retarded by the dense ligaments as the needle is inserted. The administrator then feels a slight "pop" as the ligamentum flavum, the layer positioned just before the epidural space, is punctured due to a slight pressure drop in the epidural space. The contents of the syringe then flow freely, gently expanding the separation of the two tissue layers. Such a procedure is highly dependent on the haptic sense of the operator and thus a simulation requires realistic motion and precise applied forces. Mechanical apparatus 25 includes these desired features and is described in greater detail below.

While one embodiment of the present invention will be discussed with reference to the needle 18, it will be appreciated that a great number of other types of objects can be used with the method and apparatus of the present invention. In fact, the present invention can be used with any physical object where it is desirable to provide a human/computer interface with one or more degrees of freedom. For example, in other simulated medical procedures, such medical tools as laparoscopes, catheters, other endoscopic surgical tools, or portions thereof, may be provided as tool 18. The shaft portion 28 can be part of the standard medical tool, or can be added as a linear member to operate in conjunction with apparatus 25. In other embodiments, the end of the shaft of the tool (such as any cutting edges) can be removed, since the end is not required for the virtual reality simulation, and is removed to prevent any potential damage to persons or property. In yet other embodiments, objects such as styluses, joysticks, screwdrivers, pool cues, wires, fiber optic bundles, mice, steering wheels, etc., can be used in place of tool 18 for different virtual reality, video game, and/or simulation applications. Another example of a user manipulatable object in use with the present invention is described with reference to FIG. 9.

The electronic interface 14 is a component of the human/computer interface apparatus 12 and couples the apparatus 12 to the computer 16. More particularly, interface 14 is used in preferred embodiments to couple the various actuators and sensors contained in apparatus 12 (which actuators and sensors are described in detail below) to computer 16. A suitable interface 14 is described in detail with reference to FIG. 7.

The electronic interface 14 is coupled to mechanical apparatus 25 of the apparatus 12 by a cable 30 and is coupled to the computer 16 by a cable 32. In other embodiments, signal can be sent to and from interface 14 and computer 16 by wireless transmission and reception. In some embodiments of the present invention, interface 14 serves solely as an input device for the computer 16. In other embodiments of the present invention, interface 14 serves solely as an output device for the computer 16. In preferred embodiments of the present invention, the interface 14 serves as an input/output (I/O) device for the computer 16. Electronic interface 14 can be provided in a separate box or housing as shown in FIG. 1, or can be included within mechanical apparatus 25 or within computer 16.

Figure 2A:
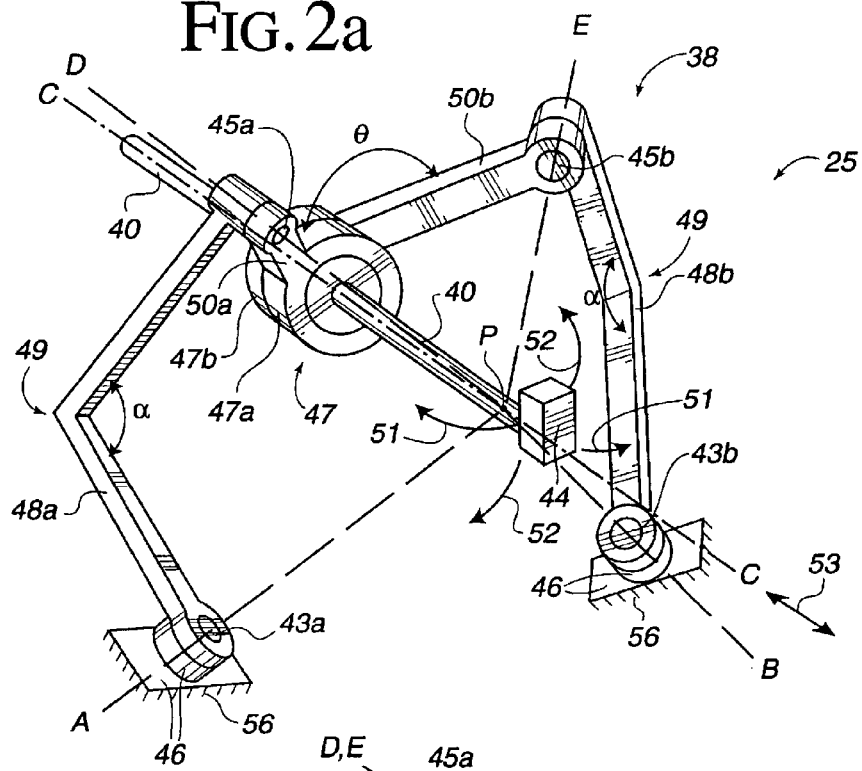
FIGS. 2a and 2b are diagrammatic views of a mechanical apparatus of the present invention for providing mechanical input and output to a computer system.

In FIG. 2*a*, a schematic diagram of mechanical apparatus 25 for providing mechanical input and output in accordance with the present invention is shown. Apparatus 25 includes a gimbal mechanism 38 and a linear axis member 40. A user object 44 is preferably coupled to linear axis member 40.

Gimbal mechanism 38, in the described embodiment, is a "spherical mechanism" that provides support for apparatus 25 on a grounded surface 56 (schematically shown as part of ground member 46). Gimbal mechanism 38 is preferably a five-member, closed loop linkage that includes a ground member 46, extension members 48*a* and 48*b*, and central members 50*a* and 50*b*. Ground member 46 is coupled to a base or surface which provides stability for apparatus 25. Ground member 46 is shown in FIG. 2 as two separate members coupled together through grounded surface 56. The members of gimbal mechanism 38 are rotatably coupled to-one another through the use of bearings or pivots, wherein extension member 48*a* is rotatably coupled to ground member 46 by bearing 43*a* and can rotate about an axis A, central member 50*a* is rotatably coupled to extension member 48*a* by bearing 45*a* and can rotate about a floating axis D, extension member 48*b* is rotatably coupled to ground member 46 by bearing 43*b* and can rotate about axis B, central member 50*b* is rotatably coupled to extension member 48*b* by bearing 45*b* and can rotate about floating axis E, and central member 50*a* is rotatably coupled to central member 50*b* by bearing 47 at a center point P at the intersection of axes D and E. Preferably, central member 50*a* is coupled to one rotatable portion 47*a* of bearing 47, and central member 50*b* is coupled to the other rotatable portion 47*b* of bearing 47. The axes D and E are "floating" in the sense that they are not fixed in one position as are axes A and B.

Gimbal mechanism 38 is formed as a five member closed chain. Each end of one member is coupled to the end of another member. The five-member linkage is arranged such that extension member 48*a*, central member 50*a*, and central member 50*b* move when extension member 48*a* is rotated about axis A in a first degree of freedom. The linkage is also arranged such that extension member 48*b*, central member 50*b*, and central member 50*a* move when extension member 48*b* is rotated about axis B in a second degree of freedom. The axes of rotation are arranged such that they intersect about at a remote pivot point P, which is the center of the "sphere" defined by the gimbal mechanism 38. Pivot point P is "remote" in the sense that it is not positioned at (or touching) any member or coupling of the gimbal mechanism 38, but is positioned in free space away from the mechanism 38 and in another "hemisphere", as explained below. Object 44 can be pivoted or rotated about pivot point P in two degrees of freedom. Extension members 48*a* and 48*b* are angled at points 49 as shown in FIG. 2*a* to allow pivot point P to be positioned remotely from the gimbal mechanism. In the described embodiment, the angles $\alpha$ are about 100 degrees, but can vary depending on how large a sphere is desired.

Linear axis member 40 is preferably an elongated rod-like member which is coupled to central member 50*a* and/or central member 50*b* and extends approximately through the remote pivot point P. As shown in FIG. 1, linear axis member 40 can be used as shaft 28 of user object 44 or 18. In other embodiments, linear axis member 40 is coupled to a separate object 44. Linear axis member 40 is coupled to gimbal mechanism 38 such that it extends out of the plane defined by axis A and axis B. Linear axis member 40 can be rotated about axis A by rotating extension member 48*a*, central member 50*a*, and central member 50*b* in a first revolute degree of freedom, shown as arrow line 51. Member 40 can also be rotated about axis B by rotating extension member 50b and the two central members about axis B in a second revolute degree of freedom, shown by arrow line 52. Being also translatably coupled to the ends of central member 50a and/or 50b, linear axis member 40 can be linearly translated, independently with respect to gimbal mechanism 38, along floating axis C, providing a third degree of freedom as shown by arrows 53. Axis C is rotated about the remote pivot point P as member 40 is rotated about this point. Optionally, a fourth degree of freedom can be provided to object 44 as rotation about axis C, i.e., a "spin" degree of freedom.

When object 44 is positioned at the "origin" as shown in FIG. 2a, an angle θ between the central members 50a and 50b is about 60 degrees in the described embodiment. When object 44 is rotated about one or both axes A and B, central members 50a and 50b move in two fashions: rotation about axis D or E by bearing 45b and/or 45a, and rotation about axis C by bearing 47 such that angle θ changes. For example, if the object 44 is moved toward the couplings 45a or 45b, then the angle θ will decrease. If the object is moved toward couplings 43a and 43b, the angle θ will increase.

Also preferably coupled to gimbal mechanism 38 and linear axis member 40 are transducers, such as sensors and actuators. Such transducers are preferably coupled at the couplings or link points between members of the apparatus and provide input to and output from an electrical system, such as computer 16. Transducers that can be used with the present invention are described in greater detail with respect to FIG. 3.

User object 44 is coupled to apparatus 25 and is preferably an interface object for a user to grasp or otherwise manipulate in three dimensional (3D) space. One preferred user object 44 is a needle 18, as shown in FIG. 1. Shaft 28 of needle 18 can be implemented as part of linear axis member 40. Needle 18 may be moved in all three degrees of freedom provided by gimbal mechanism 38 and linear axis member 40. As user object 44 is rotated about pivot point P and axis A, floating axis D varies its position, and as user object 44 is rotated about point P and axis B, floating axis E varies its position. Other types of user objects 44 can also be provided for use with mechanical apparatus 25 as described above. Other embodiments for an interface apparatus are found in co-pending U.S. Pat. No. 5,731,804, filed Jan. 18, 1995, assigned to the assignee of the present invention and incorporate herein by reference in its entirety.

Thus, the mechanical apparatus 25 fulfills the needs of an epidural anesthesia simulator by providing three degrees of freedom to user object 44: one degree of freedom for linear translation of user object along axis C to simulate needle insertion, and two degrees of freedom for angular positioning of user object about axes A and B to simulate needle orientation. For example, after a needle is inserted in the virtual patient, the operator may determine that the needle has been inserted incorrectly. The needle should then be withdrawn and repositioned by pivoting the needle as allowed by the gimbal mechanism 38. Such degrees of freedom are also useful in a variety of other applications, described subsequently. Importantly, gimbal mechanism 38 provides a remote pivot point P that is not touching any portion of the gimbal mechanism. This allows, for example, the mechanism 25 to be entirely placed behind a barrier 22 as shown in FIG. 1.

Figure 2B:
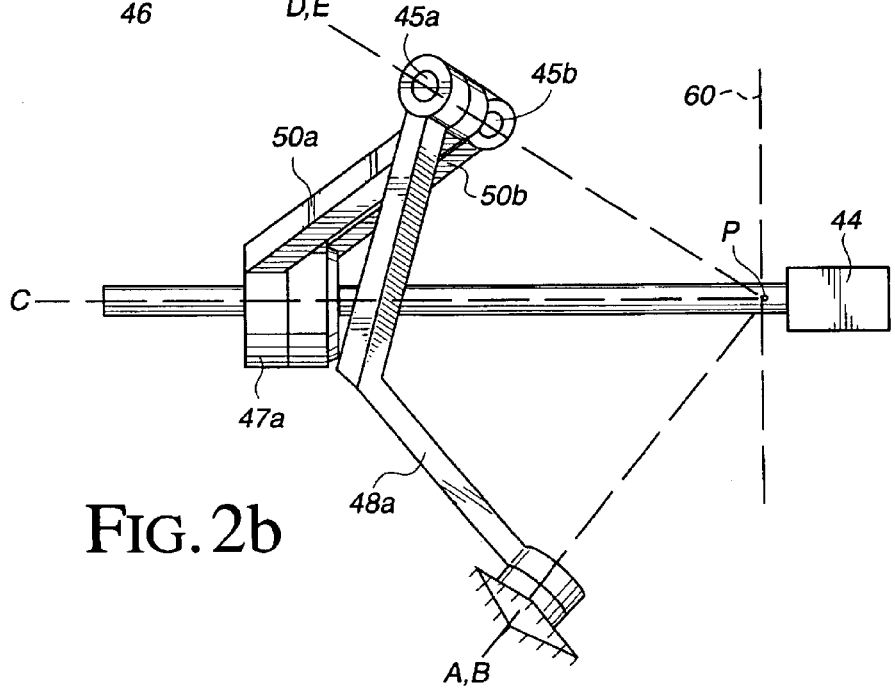

FIG. 2b is a schematic drawing of a side view of the mechanical apparatus 25 of FIG. 2a. In FIG. 2b, linear axis member 40 is shown movable along axis C. Remote pivot point P is located at the intersection of axes A, B, D, and E of the gimbal mechanism. The closed-loop five-member gimbal mechanism 38 is a "spherical mechanism", which, as described herein, is a mechanism that provides two rotational degrees of freedom to the user object 44 and a spherical workspace and in which the axes of rotation of the mechanism pass through the center of the sphere defined by the spherical workspace, i.e., user object 44 can be moved to points in 3-D space that sweep a surface, or a portion of the surface, of a sphere. For gimbal mechanism 38, the center of the sphere is remote pivot point P. With the addition of a third linear degree of freedom, the gimbal mechanism allows the user object to trace a volume of a sphere rather than just a surface of a sphere.

Unlike typical spherical mechanisms used for user interface applications, gimbal mechanism 38 includes a remote pivot point P that does not touch any portion of the gimbal mechanism. Thus, it is possible to make gimbal mechanism 38 a "hemispherical mechanism", i.e., the gimbal mechanism 38 is positioned entirely within one hemisphere of the sphere. This is demonstrated by dashed line 60, which designates a line extending through the center of a sphere, which is at pivot point P. The entire gimbal mechanism 38 is on one side of line 60, while the user manipulable object 44 is on the other side of point P and line 60 (except, of course, shaft 28, which must connect the user object 44 with the mechanical apparatus 25). This allows user object 44 a full range of movement in its own hemisphere without being obstructed by any portions of the mechanical apparatus 25.

The hemispherical nature of gimbal mechanism 38 allows a realistic simulation apparatus to be provided. For example, a barrier 20 such as shown in FIG. 1 can be placed at or near the pivot point P so that the entire mechanical apparatus 25 is hidden from view and protected. This allows an operator to easily place a hand on the barrier to support, the needle insertion without touching the gimbal mechanism. Also, since pivot point P of the shaft 28 of the needle is provided at the point of needle insertion, the needle can be pivoted without requiring a large opening in the barrier. The operation of the mechanism 25 can be completely obscured from the operator without hindering the motion of the user object 44, thus greatly adding to the realism of the simulated medical procedure.

The apparatus 25 can also be used for other applications besides the simulation of medical procedures such as epidural anesthesia. One application can be games or virtual reality (non-medical) simulations, where user object 44 can be a joystick or other object for manipulating 2- or 3-D environments. In addition, any apparatus that can make use of a gimbal mechanism that is contained within one side or hemisphere of the sphere or which can be fully enclosed behind a plane or surface is applicable to the present invention. One such apparatus might be a mechanism that is positioned below ground or under/behind a protective enclosure and which is used to direct a laser beam or projectile (e.g., a liquid projectile such as water from a water hose, or a solid projectile). For example, a laser may include a mechanical apparatus 25 that is positioned behind its pivot point P and can be used to digitize or project 3-D images using spherical coordinates of the gimbal mechanism. Alternatively, a real medical instrument can be attached to the gimbal mechanism for performing operations on live patients under computer computer or under remote control from a doctor using a master implement (e.g., the master implement can also be a gimbal mechanism of the present invention to allow teleoperation of the operating instrument).

FIG. 3 is a perspective view of a specific embodiment of a mechanical apparatus 25' for providing mechanical input and output to a computer system in accordance with the present invention. Apparatus 25' includes a gimbal mechanism 62, a linear axis member 64, and transducers 66. A user object 44, shown in this embodiment as a needle 18, is coupled to apparatus 25'. Apparatus 25' operates in substantially the same fashion as apparatus 25 described with reference to FIGS. 2a and 2b.

Figure 4A:
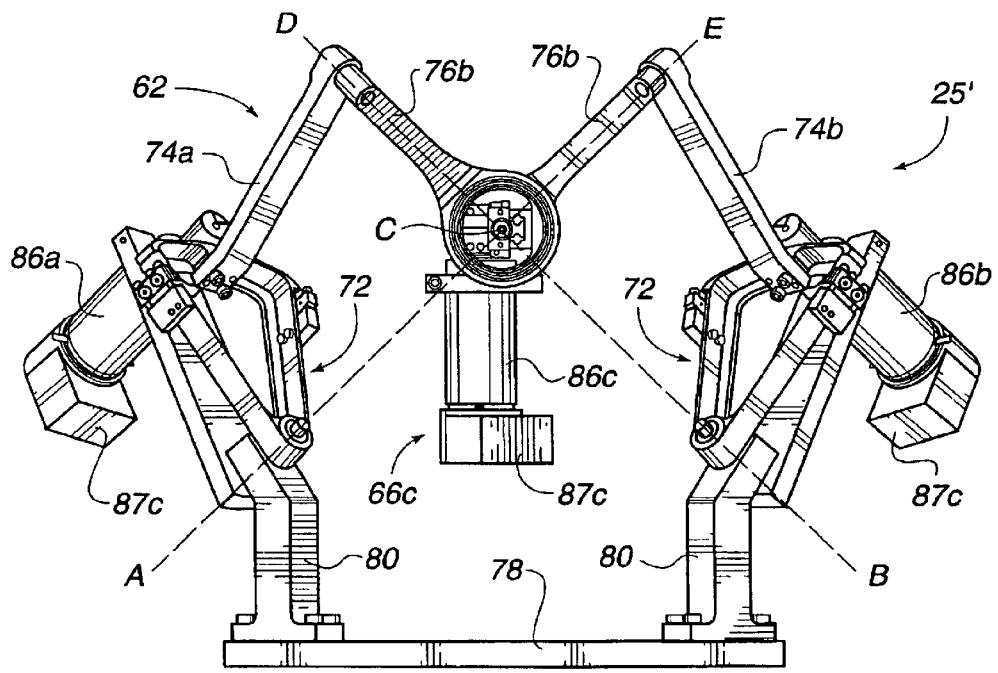
FIGS. 4a and 4b are side elevation and top plan views, respectively, of the mechanical apparatus of FIG. 3.
Figure 4B:
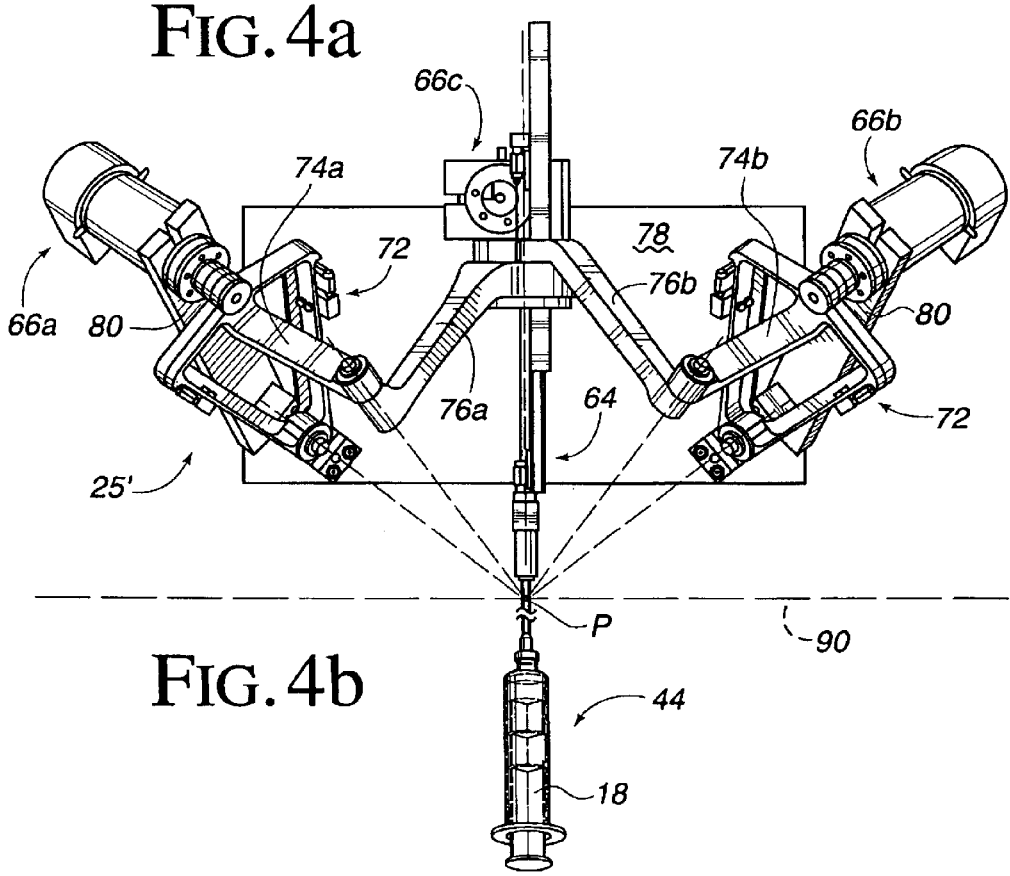

Gimbal mechanism 62 provides support for apparatus 25' on a grounded surface 56, such as a table top or similar surface. The members and joints ("bearings") of gimbal mechanism 62 are preferably made of a lightweight, rigid, stiff metal, such as aluminum, but can also be made of other rigid materials such as other metals, plastic, etc. Gimbal mechanism 62 includes a ground member 70, capstan band drive mechanisms 72, link members 74a and 74b, central members 76a and 76b. Ground member 62 includes a base member 78 and support members 80. Base member 78 is coupled to grounded surface 56. Support members 80 are coupled to base member 78 and are preferably angled as shown in FIGS. 3, 4a, and 4b.

A capstan band drive mechanism 72 is preferably coupled to each support member 62. Capstan band drive mechanisms 72 are included in gimbal mechanism 62 to provide mechanical advantage without introducing friction and backlash to the system. A drum 82 of each band drive mechanism is rotatably coupled to a corresponding support member 80 to form axes of rotation A and B, which correspond to axes A and B as shown in FIG. 1. The capstan band drive mechanisms 72 are described in greater detail with respect to FIGS. 5a and 5b.

Link member 74a is rigidly coupled to capstan drum 82a and is rotated about axis A as drum 82a is rotated. Likewise, link member 74b is rigidly coupled to drum 82b and can be rotated about axis B. Thus, in apparatus 25', link member 74a and drum 82a together form the extension member 48a shown in FIG. 2a, and link member 74b and drum 82b together form the extension member 48b. Central member 76a is rotatably coupled to the other end of link member 74a. Similarly, central member 76b is rotatably coupled to the end of link member 74b. Central members 76a and 76b are rotatably coupled to each other at their other ends at a bearing 84, through which axis C preferably extends. A floating axis of rotation D is located at the coupling of link member 74a and central member 76a, and a floating axis of rotation E is located at the coupling of link member 74b and central member 76b. A pivot point P is provided at the intersection of axes A, B, D, and E.

Gimbal mechanism 62 provides two degrees of freedom to an object positioned at or coupled to the remote pivot point P. An object 44 can be rotated point P in the degrees of freedom about axis A and B or have a combination of rotational movement about these axes. As explaind above, point P is located remote from gimbal mechanism 62 such that point P does not touch any portion of the gimbal mechanism 62.

Linear axis member 64 is a member that is preferably coupled to central member 76b. Alternatively, member 64 can be coupled to central member 76a. Member 64 extends through a open-aperture in the center of bearing 84 and through apertures in the ends of central members 76a and 76b. The linear axis member can be linearly translated along axis C, providing a third degree of freedom to user object 44 coupled to the linear axis member. Linear axis member 64 (or a portion thereof) can preferably be translated by a transducer 66c using a capstan band drive mechanism. The translation of linear axis member 64 is described in greater detail with respect to FIGS. 6a–6b.

Transducers 66a, 66b, and 66c are preferably coupled to gimbal mechanism 62 to provide input and output signals between mechanical apparatus 25' and computer 16. In the described embodiment, transducer 66a includes a grounded actuator 86a and a sensor 87a, transducer 66b includes a grounded actuator 86b and a sensor 87b, and central transducer 66c includes an actuator 86c and a sensor 87c. The housing of grounded transducer 66a is preferably coupled to a support member 80 and preferably includes both an actuator for providing force or resistance in the first revolute degree of freedom about point P and axis A and a sensor for measuring the position of object 44 in the first degree of freedom about point P and axis A, i.e., the transducer 66a is "associated with" or "related to" the first degree of freedom. A rotational shaft of actuator 66a is coupled to a spindle of capstan band drive mechanism 72 to transmit input and output along the first degree of freedom. The capstan band drive mechanism 72 is described in greater detail with respect to FIGS. 5a–5c. Grounded transducer 66b preferably corresponds to grounded transducer 66a in function and operation. Transducer 66b is coupled to the other support member 80 and is an actuator/sensor which influences or is influenced by the second revolute degree of freedom about point P and axis B.

Sensors 87a, 87b, and 87c are preferably relative optical encoders which provide signals to measure the angular rotation of a shaft of the transducer. The electrical outputs of the encoders are routed to computer interface 14 by buses (not shown) and are detailed with reference to FIG. 7. For example, 500 count encoders such as the HP-HEDS-5500-A02 from Hewlett-Packard can be used, or other encoders having higher resolution. Other types of sensors can also be used, such as potentiometers, etc. In addition, it is also possible to use non-contact sensors at different positions relative to mechanical apparatus 25. For example, a Polhemus (magnetic) sensor can detect magnetic fields from objects; or, an optical sensor such as lateral effect photo diode includes a emitter/detector pair that detects positions of the emitter with respect to the detector in one or more degrees of freedom. These types of sensors are able to detect the position of object 44 in particular degrees of freedom without having to be coupled to a joint of the mechanical apparatus. Alternatively, sensors can be positioned at other locations of relative motion or joints of mechanical apparatus 25'.

It should be noted that the present invention can utilize both absolute and relative sensors. An absolute sensor is one which the angle of the sensor is known in absolute terms, such as with an analog potentiometer. Relative sensors only provide relative angle information, and thus require some form of calibration step which provide a reference position for the relative angle information. The sensors described herein are primarily relative sensors. In consequence, there is an implied calibration step after system power-up wherein the sensor's shaft is placed in a known position within the apparatus 25' and a calibration signal is provided to the system to provide the reference position mentioned above. All angles provided by the sensors are thereafter relative to that reference position. Such calibration methods are well known to those skilled in the art and, therefore, will not be discussed in any great detail herein.

The actuators 86a, 86b, and 86c of transducers 66 can be of two types: active actuators and passive actuators. Active actuators include linear current control motors, stepper motors, pneumatic/hydraulic active actuators, and other types of actuators that transmit a force to move an object. For example, active actuators can drive a rotational shaft about an axis in a rotary degree of freedom, or drive a linear shaft along a linear degree of freedom. Active transducers of the present invention are preferably bidirectional, meaning they can selectively transmit force along either direction of a degree of freedom. For example, DC servo motors can receive force control signals to control the direction and torque (force output) that is produced on a shaft. In the described embodiment, active linear current control motors, such as DC servo motors, are used. The control signals for the motor are produced by computer interface 14 on control buses (not shown) and are detailed with respect to FIG. 7. The motors may include brakes which allow the rotation of the shaft to be halted in a short span of time. Also, the sensors and actuators in transducers 66 can be included together as sensor/actuator pair transducers. A suitable transducer for the present invention including both an optical encoder and current controlled motor is a 20 W basket wound servo motor manufactured by Maxon. In other embodiments, all or some of transducers 66 can include only sensors to provide an apparatus without force feedback along designated degrees of freedom.

In alternate embodiments, other types of motors can be used, such as a stepper motor controlled with pulse width modulation of an applied voltage, pneumatic motors, brushless DC motors, pneumatic/hydraulic actuators, a torquer (motor with limited angular range), or a voice coil. Stepper motors and the like are not as well suited because stepper motor control involves the use of steps or pulses which can be felt as pulsations by the user, thus corrupting the virtual simulation. The present invention is better suited to the use of linear current controlled motors, which do not have this noise.

Passive actuators can also be used for actuators 86a, 86b, and 8c. Magnetic particle brakes, friction brakes, or pneumatic/hydraulic passive actuators can be used in addition to or instead of a motor to generate a passive resistance or friction in a degree of motion. However, active actuators are often preferred for simulations of medical procedures, since the force of tissue on a medical instrument can often cause a "springy" feel which cannot be simulated by passive actuators. In addition, passive actuators also cannot provide gravity compensation (as described below), inertial compensation, and/or frictional compensation forces. Although an alternate embodiment only including passive actuators may not be as realistic as an embodiment including motors, the passive actuators are typically safer for a user since the user does not have to fight generated forces. Passive actuators typically can only provide bi-directional resistance to a degree of motion. A suitable magnetic particle brake for interface device 14 is available from Force Limited, Inc. of Santa Monica, Calif.

Central transducer 66c is coupled to central link member 76b and preferably includes an actuator 86c for providing force in the linear third degree of freedom along axis C and a sensor 87c for measuring the position of object 44 along the third linear degree of freedom. The shaft of central transducer 88 is coupled to a translation interface coupled to central member 76b which is described in greater detail with respect to FIGS. 6a–6b. In the described embodiment, central transducer 66c is an optical encoder and DC servo motor combination similar to the transducers 66a and 66b described above. In an alternate embodiment, transducer 66c can be coupled to ground 56 using, for example, a flexible transmission system such as a shaft or belt between a drive spindle 92 (shown in FIG. 5a) and the transducer 66c. Such an embodiment is advantageous in that the weight of transducer 66c is not carried by the user when manipulating object 44.

The transducers 66a and 66b of the described embodiment are advantageously positioned to provide a very low amount of inertia to the user handling object 44. Transducer 66a and transducer 66b are decoupled, meaning that the transducers are both directly coupled through supports 80 to ground member 70, which is coupled to ground surface 56, i.e., the ground surface carries the weight of the transducers, not the user handling object 44. The weights and inertia of the transducers 66a and 66b are thus substantially negligible to a user handling and moving object 44. This provides a more realistic interface to a virtual reality system, since the computer can control the transducers to provide substantially all of the forces felt by the user in these degrees of motion. Apparatus 25' is a high bandwidth force feedback system, meaning that high mechanical stiffness is provided for realistic forces and that high frequency signals can be used to control transducers 66 and these high frequency signals will be applied to the user object with high precision, accuracy, and dependability. The user feels very little compliance or "mushiness" when handling object 44 due to the high bandwidth. In contrast, in many,prior art arrangements of multi-degree of freedom interfaces, one actuator "rides" upon another actuator in a serial chain of links and actuators. This low bandwidth arrangement causes the user to feel the inertia of coupled actuators when manipulating an object.

In other embodiments, the linear axis member can include additional sensors and/or actuators for measuring the position of and providing forces to object 44 in additional degrees of freedom. For example, a shaft transducer can be positioned on linear axis member 64 to measure the rotational position of object 44 about axis C in a fourth "spin" degree of freedom. The transducer can be an optical encoder as described above. For typical medical procedures, which is one intended application for the embodiment shown in FIGS. 3 and 4, rotational force feedback to a user about axis C is typically not required to simulate actual operating conditions. However, in alternate embodiments, an actuator such as a motor can be included in such a shaft transducer similar to transducers 86a, 86b, and 88 to provide forces on object 44 in the fourth degree of freedom.

Object 44 is shown in FIG. 3 as a needle 18 as shown in FIG. 1. Shaft portion 28 is coupled to and included as linear axis member 64. An adapter can be provided to engage the shaft 28 with the linear axis member 64 of the mechanism. A user can rotate the needle 18 about point P on axes A and B, and can translate the needle along axis C through point P. The movements in the three degrees of freedom will be sensed and tracked by computer system 16. Forces can be applied preferably in the three degrees of freedom by the computer system to simulate the tool impacting a portion of the subject body, experiencing resistance moving through tissues, etc. Optionally, a user also can spin needle 18 about axis C in a fourth degree of freedom.

FIG. 3 also shows a plunger actuation mechanism 88 for providing forces on plunger 27 of needle 18. In the described embodiment, an additional actuator 89 is coupled to a needle mount 91 on linear axis member 64 by a hose 93. Preferably, actuator 89 is a binary solenoid valve that either allows a fluid (e.g., a liquid or gas) to flow (when open) or blocks the flow of fluid (when closed). For example, a clippard minimatic ET-2-12 valve is suitable. The valve 89 is coupled to computer 16 by a bus and may be opened or closed by the computer 16. A passage is provided from the interior of needle 18, through shaft 28, through needle mount 91, and through hose 93. Thus, the computer can open or close valve 89 to allow a fluid to flow to release pressure on the plunger 27 or to block fluid flow and provide a feeling of pressure on the plunger 27. The binary valve allows the apparatus 25' to simulate the condition of pressure on plunger 27 in an epidural anesthesia procedure, where the pressure is typically close to being either "on" (before the space where fluid is injected is reached) or "off" (when the needle has reached the space to inject fluid). A reservoir (not shown) can be added to the valve to handle liquid flow. In alternate embodiments, a valve allowing variable control of fluid flow can be provided. In other embodiments, an active actuator can be coupled to needle 18 to actively simulate the flow of a fluid through the needle, i.e., no fluid need actually be provided, since the actuator could provide forces that feel as if a liquid were present. For example, a linear actuator such as a linear voice coil can be used. In yet other embodiments, a sensor can be provided to track the position of the plunger 27 relative to the housing 29 and/or to detect when the user pushes or pulls on the plunger.

Optionally, additional transducers can be added to apparatus 25' to provide additional degrees of freedom for object 44. A laparoscopic tool and catheter is described in copending U.S. Pat. No. 5,623,582, filed Jul. 14, 1994, and U.S. Pat. No. 5,821,920, filed Nov. 23, 1994, both assigned to the assignee of the present invention and incorporated herein by reference in their entirety. In yet other embodiments, flexible members and/or couplings can be used in the embodiment of FIG. 2a or 3, as described in copending U.S. Pat. No. 5,805,140, filed Nov. 17, 1995, and hereby incorporated by reference herein.

In an alternate embodiment, the gimbal mechanism 62 can be omitted and a single linear degree of freedom along axis C can be provided for the user object 44. For example, in some epidural anesthesia simulations, the angular positioning of the needle 18 may not be needed, and only the insertion and retraction of the needle can be simulated. In such an embodiment, the linear axis member 64 and transducer 86c can be used to provide forces in the linear degree of freedom. (e.g., the chassis 124 of the linear axis member 64 can be mounted to ground and the needle 18 can be translated along the one degree of freedom allowed by slide 64).

FIGS. 4a and 4b are a front elevation view and a top plan view, respectively, of mechanical apparatus 25' of FIG. 3. In FIG. 4a, it is shown that axes A and E are aligned when viewing them from the front, as are axes B and D. In the top plan view of FIG. 4b, user object 44 (in this case needle 18) is shown coupled to linear axis member 64. Pivot point P is positioned remotely from mechanical apparatus 25' such that the apparatus 25' is positioned entirely on one side of the pivot point P and user object 44 is positioned on the other side of the pivot point as demonstrated by dashed line 90.

Figure 5A:
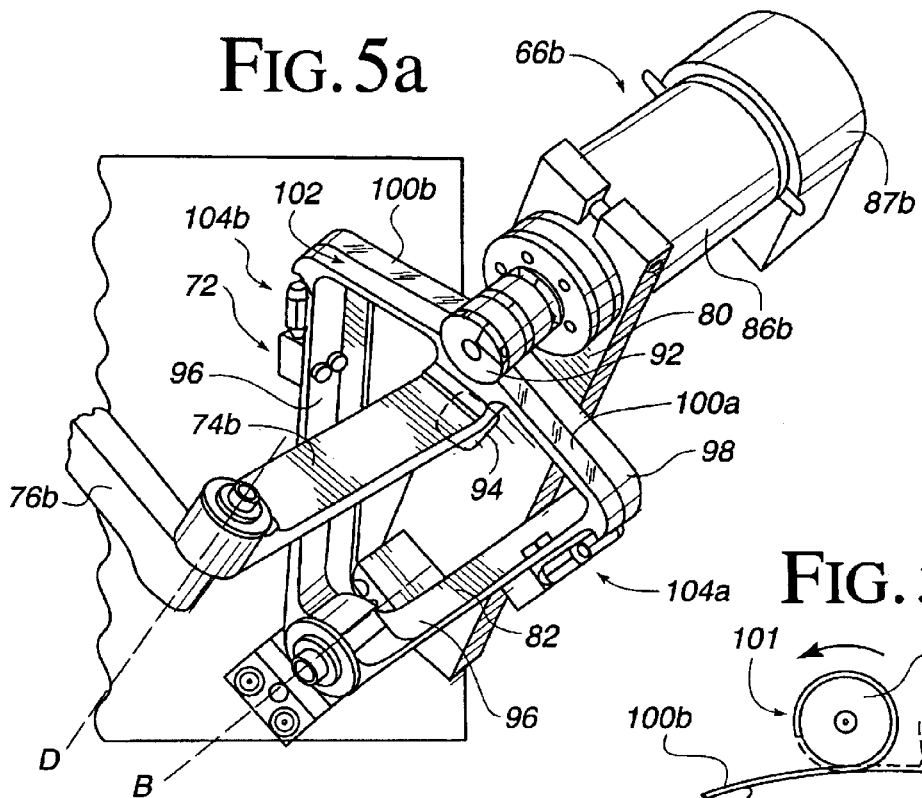
FIGS. 5a, 5b and 5c are detailed views of a capstan band drive mechanism used in the present invention.

FIG. 5a is a perspective view of a capstan band drive mechanism 72 of the present invention shown in some detail. As an example, the drive mechanism 72 coupled to link member 74b is shown; the other capstan drive 72 coupled to link member 74a is substantially similar to the mechanism presented here. Capstan band drive mechanism 72 includes drum 82, spindle (or "capstan") 92, and stop 94. Drum 82 is preferably a wedge-shaped member having leg portion 96 and a curved portion 98. Other shapes of drum 82 can also be used. Leg portion 96 is pivotally coupled to support member 80 at axis B (or axis A for the other band drive mechanism 72). Curved portion 84 couples the two ends of leg portion 82 together and is preferably formed in an arc centered about axis B. Curved portion 84 is preferably positioned such that its bottom edge 86 is about 0.030 inches below spindle 92. Link member 74b is rigidly coupled to curved portion 98 such that when drum 82 is rotated about axis B, link member 74b is also rotated.

Spindle 92 is a cylindrically-shaped roller rigidly coupled to a shaft of actuator 86b that is used to transfer torque to and from actuator 86b. In a preferred embodiment, spindle 92 is about 0.75" in diameter, but can be other sizes in other embodiments. Bands 100a and 100b are preferably thin metal bands, made of materials such as stainless steel, and which are connected to spindle 92. For example, ¼" wide and 0.0005" or 0.001" thick bands are suitable for the present invention. Band 100a is attached at a first end to spindle 92, is drawn tightly against the outer surface 102 of curved portion 98, and is coupled at its other end to a leg portion 96 by a fastener 104a. Likewise, band 100b is attached at a first end to spindle 92, offset from band 100a on the spindle. Band 100b is wrapped around spindle 92 in the opposite direction to band 100a, is drawn in the opposite direction to band. 100a tightly against the outer surface 102 of curved portion 98, and is coupled at its other end to a leg portion 96 by a fastener 104b.

Figure 5B:
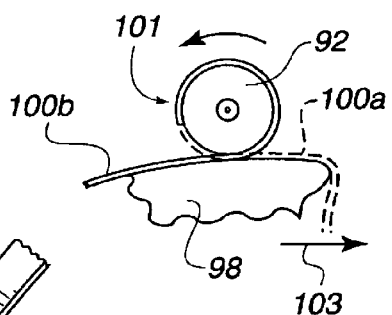

Spindle 92 is rotated by actuator 86b, and bands 100a and 100b transmit the rotational force from spindle 92 to the drum 82, causing drum 82 to rotate about axis B. As shown in FIG. 5b, band 100b is attached to spindle 92 at point 101, is wrapped around the spindle clockwise, and is extended along the surface of curved portion 98. Thus, when the spindle 92 is rotated in a counterclockwise direction by actuator 86a, then band 100b pulls on one side of drum 82, thus rotating the drum clockwise about axis B as shown by arrow 103. The bands 100a and 100b also transmit rotational position (e.g., when the user object is moved by the user) from drum 82 to the spindle 92 and thus to sensor 87b so that the position of the user object is sensed. The tension in bands 100a and 100b should be at a high enough level so that negligible backlash or play occurs between drum 82 and spindle 92. Preferably, the tension of bands 100a and 100b can be adjusted by pulling more (or less) band length through fastener 104 and 104b, as explained below in FIG. 5c.

Spindle 92 is a metal cylinder which transfers rotational force from actuator 86b to capstan drum 82 and from capstan drum 82 to sensor 87b. Spindle 92 is rotationally coupled to transducer 66b by a shaft (not shown), and the transducer is rigidly attached to support member 80. Rotational force (torque) is applied from actuator 86b to spindle 92 when the actuator rotates the shaft. The spindle, in turn, transmits the rotational force to bands 100a and 100b and thus forces capstan drum 82 to rotate in a direction about axis B. Link member 74b rotates with drum 82, thus causing force along the second degree of freedom for object 44. Note that spindle 92, capstan drum 82 and link member 74b will only physically rotate if the user is not applying the same amount or a greater amount of rotational force to object 44 in the opposite direction to cancel the rotational movement. In any event, the user will feel the rotational force along the second degree of freedom in object 44 as force feedback.

Stop 106 is rigidly coupled to support member 80 below curved portion 98 of capstan drum 82. Stop 106 is used to prevent capstan drum 82 from moving beyond a designated angular limit. Thus, drum 82 is constrained to movement within a range defined by the arc length between the ends of leg portion 96. This constrained movement, in turn, constrains the movement of object 44 in the first two degrees of freedom. In the described embodiment, stop 106 is a cylindrical member inserted into a threaded bore in support member 80 and is encased in a resilient material, such as rubber, to prevent impact damage with drum 82.

The capstan drive mechanism 72 provides a mechanical advantage to apparatus 25' so that the force output of the actuators can be increased. The ratio of the diameter of spindle 92 to the diameter of capstan drum 82 (i.e., double the distance from axis B to the edge 102 of capstan drum 82) dictates the amount of mechanical advantage, similar to a gear system. In the described embodiment, the ratio of drum to spindle is equal to 15:1, although other ratios can be used in other embodiments.

Similarly, when the user moves object 44 in the second degree of freedom, link member 74b rotates about axis B and rotates drum 82 about axis B as well. This movement causes bands 100a and 100b to move, which transmits the rotational force/position to spindle 92. Spindle 92 rotates and causes the shaft of actuator 86a to rotate, which is also coupled to sensor 87b. Sensor 87b thus can detect the direction and magnitude of the movement of drum 82. A similar process occurs along the first degree of freedom for the other band drive mechanism 72. As described above with respect to the actuators, the capstan band drive mechanism provides a mechanical advantage to amplify the sensor resolution by a ratio of drum 82 to spindle 92 (15:1 in the described embodiment).

In alternate embodiments, a single band can be used instead of two bands 100a and 100b. In such an embodiment, the single band would be attached at one fastener 104a, drawn along surface 102, wrapped around spindle 92, drawn along surface 102, and attached at fastener 104b.

In alternate embodiments, a capstan cable drive can be used, where a cable, cord, wire, etc. can provide the drive transmission from actuator to user object. This embodiment is described in greater detail in co-pending patent application Ser. No. 08/374,288. The cable 80 is wrapped around the spindle a number of times and is then again drawn tautly against outer surface 102. The second end of the cable is firmly attached to the other end of the curved portion near the opposite leg of leg portion 96.

Band drive mechanism 72 is advantageously used in the present invention to provide high bandwidth transmission of forces and mechanical advantage between transducers 66a and 66b and object 44 without introducing substantial compliance, friction, or backlash to the system. A capstan drive provides increased stiffness, so that forces are transmitted with negligible stretch and compression of the components. The amount of friction is also reduced with a band drive mechanism so that substantially "noiseless" tactile signals can be provided to the user. In addition, the amount of backlash contributed by a band drive is negligible. "Backlash" is the amount of play that occurs between two coupled rotating objects in a gear or pulley system. Gears other types of drive mechanisms could also be used in place of band drive mechanism 72 in alternate embodiments to transmit forces between transducer 66a and link member 74b. However, gears and the like typically introduce some backlash in the system. In addition, a user might be able to feel the interlocking and grinding of gear teeth during rotation of gears when manipulating object 44; the rotation in a band drive mechanism is much less noticeable.

The use of bands 100a and 100b in a force feedback interface mechanism provides higher performance than other drive transmission systems such as the cable drive described in co-pending patent application Ser. No. 08/374, 288. Since each band 100a and 100b is attached to spindle 92, the tension of the bands does not need to be as high as in a system having one cable or band that stretches from fastener 104a to 104b. Thus, considerable assembly time is saved when using bands 100a and 100b rather than a cable.

There is also energy loss associated with cable deflection as the capstan turns which is minimized in the band drives of the present invention.

When using a band drive system as described, the bands wrap around themselves on spindle 92, i.e., the spindle in effect grows in circumference. Band stretch is thus of possible concern; however, the stretch has been found to be well within the limits of the strain capabilities of the bands. In addition, there is a tendency for the drum 82 to spring back to the center of travel, where the band stretch is at its lowest. However, there are several,ways to compensate for this spring effect. In the preferred embodiment, control software implemented by the computer 16 compensates for the stretch springiness by computing an equal and opposite force to the spring force based, for example, on a spring constant of the band or a value from a look up table. In other embodiments, the bands 100a and 100b can be wrapped diagonally on spindle 92 so that the bands never wrap around themselves. However, this requires a wider spindle and a less compact mechanism. Alternatively, a spring can be provided on spindle 92 to compensate for the stretch of the bands 100a and 100b.

Figure 5C:
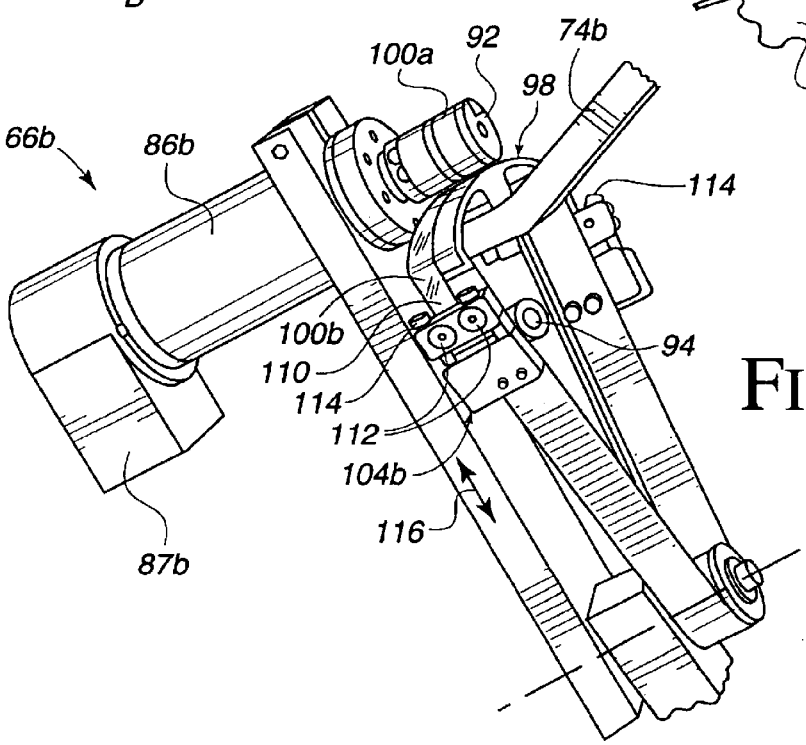

FIG. 5c is a detail perspective view of band drive mechanism 72. Band 100b is shown routed on curved portion 98 of drum 82 between spindle 92 and fastener 104b. In the described embodiment, fastener 104b is a clamp which holds the end 110 of band 100b as controlled by tension. The tension between the clamp is controlled by tension screws 112. In addition, the fastener 104b can preferably be moved in either direction shown by arrow 116 to further tighten the band 100b. In the described embodiment, tension screws 114 can be adjusted to move the fastener in either direction as desired.

Figure 6A:
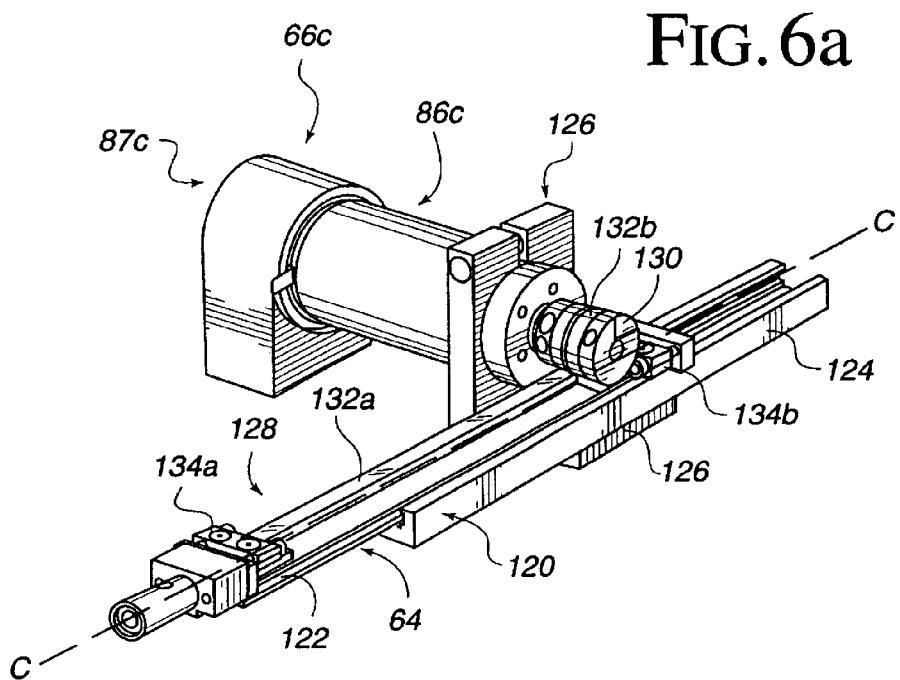
FIGS. 6a and 6b are perspective views of a capstan band drive mechanism for a linear axis member of the mechanical apparatus of FIG. 3.
Figure 6B:
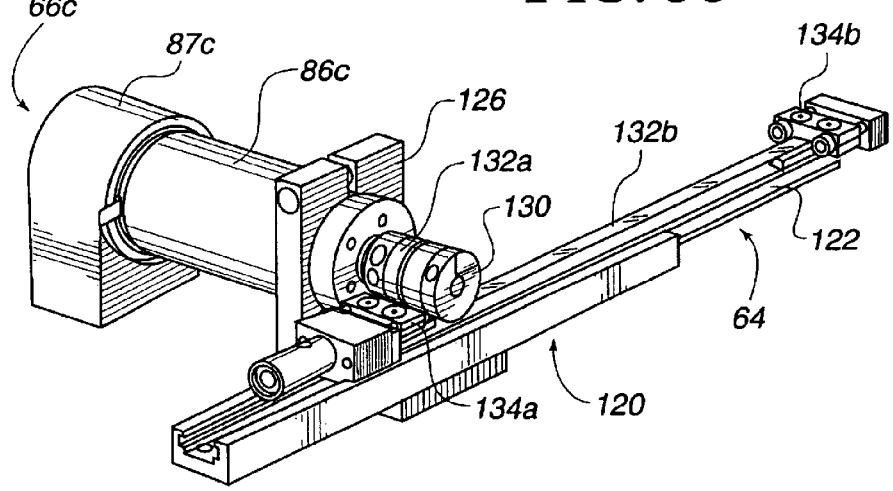

FIGS. 6a and 6b are perspective views of linear axis member 64 and central transducer 66c shown in some detail. In the described embodiment, linear axis member 64 is implemented as a moving slide in a linear bearing 120. Linear bearing 120 includes slide 122 and exterior chassis 124. In the described embodiment, linear bearing 120 is a ball slide bearing that allows slide 122 to linearly translate within chassis 124 with minimal friction. A suitable ball slide linear bearing is available from Detron Precision, Inc. Other types of linear bearings can be used in other embodiments, such as Rolamite bearings, crossed roller linear bearings, and recirculating ball linear bearings.

Central transducer 66c is coupled to the linear bearing 120 by a mount 126. Mount 126 is also coupled to one of the central members 74a or 74b to attach the linear axis member 64 to the gimbal mechanism 62. In the described embodiment, a capstan band drive mechanism128 is used to transmit forces between transducer 66c and slide 122 along the linear third degree of freedom. A spindle 130 is coupled to the shafts of the actuator 86c and sensor 87c such that the spindle is positioned just above the slide 122, and is similar to spindle 92 of capstan band drive mechanism 72 shown in FIG. 5a. A band 132a is coupled at one end to spindle 130, is wrapped around the spindle, is routed along the ball slide 122, and is tightly secured at its other end to fastener 134a, which is coupled to the slide 122. Likewise, band 132b is coupled at one end to spindle 130 offset from band 132a, is wrapped around spindle 130 in the opposite direction to band 132a, is routed along the opposite direction to band 132a on the slide, and is secured at fastener 134b, which is coupled to the slide 122 (band 132b is better shown in FIG. 6b). The bands 132a and 132b and spindle 130 operate similarly to the band drive of FIG. 5a to provide a very smooth, low friction, high bandwidth force transmission system for precise movement of linear axis member 64 and accurate position measurement of the member 64. FIG. 6a shows the limit to the slide 122 movement at one end of the movement range, and FIG. 6b shows the limit of the slide movement at the other end of the range. Fasteners 134a and 134b are preferably clamps similar to the clamps described for FIG. 5a.

Using the capstan band drive mechanism 128, transducer 66c can translate linear axis member 64 (slide 122) along axis C when the spindle is rotated by the actuator 86c. Likewise, when linear axis member 64 is translated along axis C by the user manipulating the object 44, spindle 130 is rotated by bands 132a and 132b; this rotation is detected by the sensor 87c.

In other embodiments, other types of drive mechanisms can be used to transmit forces to linear axis member and receive positional information from member 64 along axis C. For example, a drive wheel made of a rubber-like material or other frictional material can be positioned on ball slide 122 to contact linear axis member 64 along the edge of the wheel and thus convert linear motion to rotary motion and vice-versa. The wheel can cause forces along member 64 from the friction between wheel and linear axis member. Such a drive wheel mechanism is disclosed in U.S. Pat. No. 5,623,582 as well as in U.S. Pat. No. 5,821,920. The drive mechanism can also be implemented in other ways, as explained above, as explained above with respect to FIG. 5a.

In yet other embodiments, a fourth degree of freedom can be provided to object 44 by sensing and/or actuating spin of linear axis member 64 about axis C.

Figure 7:
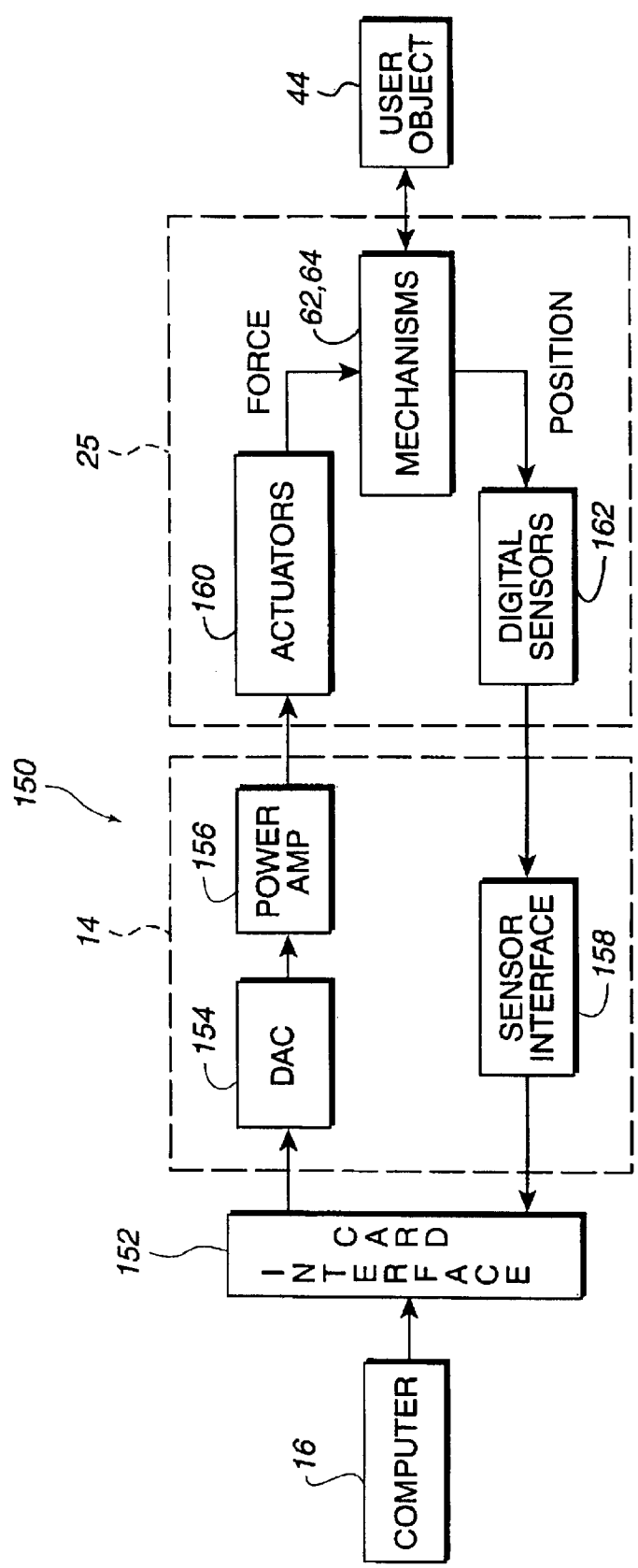
FIG. 7 is a block diagram of a computer and the interface between the computer and the mechanical apparatus of FIGS. 2 and 3.

FIG. 7 is a block diagram a computer 16 and an interface circuit 150 used in interface 14 to send and receive signals from mechanical apparatus 25. The interface circuit includes an interface card 152, DAC 154, power amplifier circuit 156, and sensor interface 158. In this embodiment, the interface 14 between computer 16 and mechanical apparatus 25 as shown in FIG. 1 can be considered functionally equivalent to the interface circuits enclosed within the dashed line in FIG. 7. Other types of interfaces 14 can also be used. For example, an electronic interface is described in U.S. Pat. No. 5,576,727, filed Jun. 5, 1995, assigned to the assignee of the present invention and incorporated herein by reference in its entirety. The electronic interface described therein has six channels corresponding to the six degrees of freedom of a mechanical linkage.

Interface card 152 is preferably a card which can fit into an interface slot of computer 16. For example, if computer 16 is an IBM AT compatible computer, interface card 14 can be implemented as an ISA, VESA, PCI or other standard interface card which plugs into the motherboard of the computer, provides input and output ports connected to the main data bus of the computer, and may include memory, interface circuitry, and the like. In alternate embodiments, no interface card 152 need be used, and a direct interface bus can be provided from interface 14 and computer 16. For example, a serial interface such as RS-232, Universal Serial Bus (USB), or Firewire can be used to connect a serial port or parallel port of computer 16 to interface 14. Also, networking hardware and protocols, such as ethernet, can also be used.

Digital to analog converter (DAC) 154 is coupled to interface card 152 and receives a digital signal from computer 16. DAC 154 converts the digital signal to analog voltages which are then sent to power amplifier circuit 156. DAC circuits suitable for use with the present invention are described in U.S. Pat. No. 5,731, 804, previously incorporated by reference. Power amplifier circuit 156 receives an analog low-power control voltage from DAC 154 and amplifies the voltage to control actuators of the mechanical apparatus 25. A suitable power amplifier circuit 156 is described in greater detail in co-pending patent application 08/374,288. Sensor interface 158 receives and converts signals from sensors 162 to a form appropriate for computer 16, as described below.

Mechanical apparatus 25 is indicated by a dashed line in FIG. 7 and includes actuators 160, sensors 162, and mechanisms 62 and 64. Actuators 160 can one or more of a variety of types of actuators, such as the DC motors 86a, 86b, and 86c, passive actuators, valve 89, and any additional actuators for providing force feedback to a user manipulated object 44 coupled to mechanical apparatus 25. The computer 16 determines appropriately scaled digital values to send to the actuators. Actuators 160 receive the computer signal as an amplified analog control signal from power amplifier 156.

Sensors 162 are preferably digital sensors that provide signals to computer 16 relating the position of the user object 44 in 3D space. In the preferred embodiments described above, sensors 162 are relative optical encoders, which are electro-optical devices that respond to a shaft's rotation by producing two phase-related signals and outputting those signals to sensor interface 158. In the described embodiment, sensor interface circuit 158 is preferably a single chip that converts the two signals from each sensor into another pair of clock signals, which drive a bidirectional binary counter. The output of the binary counter is received by computer 16 as a binary number representing the angular position of the encoded shaft. Such circuits, or equivalent circuits, are well known to those skilled in the art; for example, the Quadrature Chip from Hewlett Packard, California performs the functions described above.

Alternatively, analog sensors can be included instead of or in addition to digital sensors 162, such as potentiometers. Or, a strain gauge can be connected to the user object 44 to measure forces. Analog sensors 132 provide an analog signal representative of the position of the user object in a particular degree of motion. In such an embodiment, sensor interface 158 includes an analog to digital converter (ADC) 134 to convert the analog sensor signal to a digital signal that is received and interpreted by computer 16, as is well known to those skilled in the art.

Mechanisms 62 and 64 interface the movement and forces between the user object 44 and the sensors and actuators. From the mechanical movement of the mechanisms 62 and 64, the computer 16 receives inputs in z(t) (linear axis), φ(t) and ψ(t) (rotational axes). Using the mechanical movement of the mechanisms 62 and 64, computer 16 outputs forces on the user object in these same degrees of freedom.

Other input devices can also be included on user object 44 or on mechanical apparatus 25 to allow the user to input additional commands. For example, buttons, levers, dials, etc. can input signals to interface 14 to inform the computer 16 when these input devices have been activated by the user.

In other embodiments, the interface 14 can be included in computer 16 or in mechanical apparatus 25. In yet other embodiments, the interface 14 can include a separate, local microprocessor that is dedicated to handling much of the force feedback functionality of the mechanical apparatus 25 independently of computer 16. Such an embodiment, and other related interface functions, are described in greater detail with respect to co-pending patent application Ser. No. 08/566,282, hereby incorporated by reference herein.

FIG. 8 is a flow diagram illustrating a process of controlling mechanical interface apparatus 25' in the simulation of an epidural anesthesia procedure. Appendix A includes an example listing of computer instructions to implement a control method for an epidural anesthesia procedure. A similar process and/or different procedures well known to those skilled in the art can be implemented in the simulation of other activities, procedures, garmes, etc., and with the use of other types of user objects 44.

When training an anesthesiologist using the simulator of the present invention, the trainee will typically practice the initial stages of the procedure on a patient or other conventional testing means, i.e., the trainee learns from an instructor how to place the patient on the operating table and locate the point of insertion about halfway between the vertebrae L4 and L5. At this point, the trainee can move over to the mechanical apparatus 25' and practice the remainder of the procedure.

When operating the mechanical interface apparatus 25', the trainee aims the needle 18 approximately 10° toward the head of the patient (which can be displayed on a computer monitor or head mounted display). When appropriate needle position is attained, needle insertion is begun. Various forces are provided on the needle as it is inserted depending on the distance and direction of travel through simulated tissue, as explained below.

The process begins at 202, and in step 204, the computer 16 and the mechanical interface apparatus 25' are powered up. Various initialization procedures can be performed at this stage for the components of the apparatus, as is well known to those skilled in the art. In step 206, the computer 16 retrieves sensor data from the sensors 162 of the interface apparatus. In the described embodiment, the computer 16 receives digital data from sensors 87a, 87b, and 87c, which are preferably rotary optical encoders. In step 208, the position and state of the needle is determined using the sensor data retrieved in step 206. The tip of shaft 28 of the needle 18 can be any designated point along shaft 28, and is preferably designated to be the point where the shaft 28 is coupled to needle mount 91. The needle tip is known to be a predetermined distance and angle from the links and members of the mechanical apparatus and its position can thus be calculated from the sensor data. The "state" of the needle includes whether the needle is advancing into the simulated tissue of the patient or being retracted from the tissue. In addition, the calculation of the angular position of each link of the apparatus 25' can be performed in this step. Although not necessary in the preferred embodiment, calculations in other embodiments can include compensations for the increased diameters of spindles 92 as the bands 100 wrap around themselves. As an example, the listing of instructions in Appendix A provides equations for calculating angular positions and other parameters for apparatus 25.

Figure 8A:
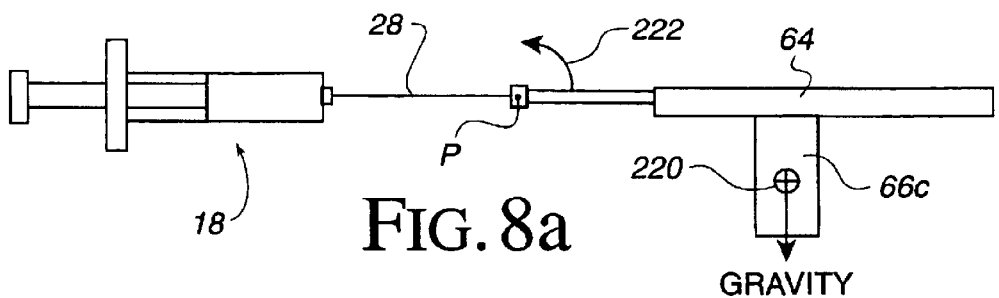
FIG. 8a is a side view of the user object and linear axis member illustrating the gravity compensation of the present invention.

In step 210, the computer calculates an amount of force (torque) that would compensate for the influence of gravity on the user object (needle) and mechanical apparatus at the detected position of the needle tip. The gravity compensation uses forces generated by actuators 86a–c to support the weight of the actuators and the mechanism to allow the needle to be manipulated free from this weight. For example, FIG. 8a illustrates the needle 18, linear axis member 64, and transducer 66c and the effect of gravity on the mechanism. Linear axis member 64 is coupled to shaft 28 of needle 18. Transducer 66c is coupled to the linear axis member 64 and is one of the heaviest components of the apparatus 25. Unlike transducers 66a and 66b, transducer 66c is not grounded and therefore the user can feel the weight of transducer 66c when manipulating needle 18. The mechanism's center of gravity is shown by point 220, where gravity causes a downward force on the mechanism. This weight causes a significant moment about the pivot point P, i.e., the needle 18 is caused to undesirably rotate about the pivot point P and, due to the flexible nature of the needle shaft 28, prevent the needle from being rotated about point P, axes A and B (as shown in FIG. 3). Thus, in step 210, the computer calculates a force 222 equal to the gravitational force of the mass on mechanism and opposite in direction to compensate for the weight of the actuator and mechanism, taking into account the current position of the needle about the axes of the mechanism. This allows the user to freely rotate the needle about point P while feeling a negligible amount of the weight of the mechanism and actuator. The compensating force is calculated according to methods and equations well known to those skilled in the art.

In step 212, the process checks whether the needle is within the simulated tissue by checking the position determined in step 208. If not, then the process returns to step 206 to update the retrieved sensor data. If the needle is within the simulated tissue, then in step 213 the force on the needle, as exerted by the simulated tissue, is calculated for use in subsequent steps. In next step 214, the process checks if the needle has the desired angular position, where the "desired" position is one in which the advancing needle will contact the epidural space of the patient and not bone or other obstructions in the simulated body. Preferably, a predetermined angular range within the workspace of the needle is checked to determine if the needle is at the desired position. If so, step 216 is performed, where the appropriate physical property profile for the desired needle trajectory is selected from memory (such as RAM or ROM included in computer 16). A "physical property profile", as discussed herein, is a collection of stored predetermined values that characterize or describe a physical structure or area at different locations. For example, the different tissue layers beneath the skin may have different characteristics and thus will act differently on an advancing needle at different depths. The physical property profile can include material stiffness values that indicate the stiffness of the tissue at particular depths. A stiffness value from the profile is used by the process to eventually determine forces on the needle interacting with the simulated tissue. In other embodiments, other or additional physical property values can be included in the profile. For example, density and texture values can be provided for different depths of a patient's tissue. In other embodiments, a physical property profile may describe physical properties of different layers of, for example, sediment which can be used to determine forces on an instrument probing for oil.

Since, in the described embodiment, different physical property profiles are used for an advancing needle and for a retracting needle, the process checks the current position and one or more previous positions of the needle to determine the needle's direction and then selects the appropriate profile. This realistically simulates the different feel on a needle when advancing vs. retracting the needle. The value in the profile that corresponds to the current position of the needle is used in the calculation of force to be output, as described below. The physical property profiles are advantageous in that they include a number of property values corresponding to different depths. Thus, to provide for patient variation, the values can be easily changed to achieve a high degree of customization to simulate different tissue resistances and different sizes/depths of tissues in different patients.

Figure 8B:
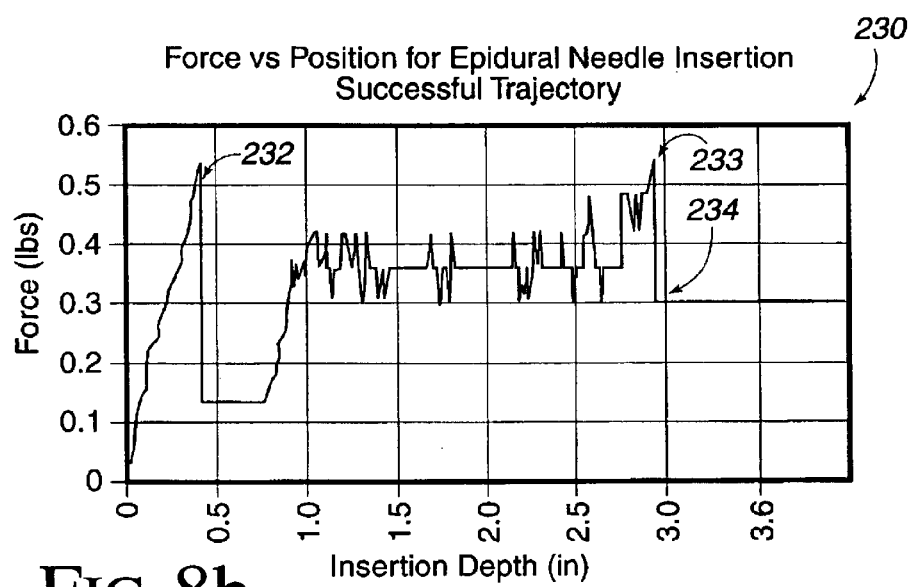
FIGS. 8b and 8c are graphs showing the force output on the needle of the apparatus of the present invention according to physical property profiles.

FIG. 8b is a graph 230 showing the force output on needle 18 using a physical property profile with respect to needle insertion depth for a desired (successful) trajectory of the needle in the simulated tissue of a patient. These forces result from a profile selected when the needle is advancing into the simulated tissue. Between and insertion depth of 0 and 0.5 inches, an initial force spike 232 is output in the direction resisting the advance of the needle, after which the force drops sharply. Spike 232 is intended to simulate the puncturing of skin by the tip of the needle shaft 28, and thus a high stiffness value (and/or other values) are stored in the profile for this insertion depth. The force resisting the needle then increases steadily with insertion depth between about 0.75 and 2.75 inches. The small spike 233 is meant to simulate the needle encountering the Ligamentum flavum directly before the epidural space, which can be a hard substance that exerts a greater force on the needle, and thus corresponds to a higher stiffness in the profile. The force then drops sharply before an insertion depth of about 2.75 to 3 inches, at point 234. This drop in force simulates the needle entering the epidural space, which is the desired space to inject the anesthetic. Once this space is reached, the simulation is complete. In alternate embodiments, the other side of the epidural space can also be simulated. For example, after about a distance of ½oth of an inch past point 234, a large force spike can be output based on a high tension value in the physical property profile, which simulates bone on the other side of the epidural space.

Referring back to FIG. 8, the process continues after step 216 to step 220, detailed below. If the needle does not have the desired or successful angular position in step 214, then step 218 is performed, where the appropriate physical property profile is selected for the needle encountering bone in the simulated body (or other obstacle), or a different "failure" profile is selected if desired. Thus, if the user angles the needle incorrectly, the needle will miss the desired epidural space and most likely will impact a bone structure. As in step 216, different profiles are available for both directions of movement of the incorrectly-angled needle in the simulated tissue.

Figure 8C:
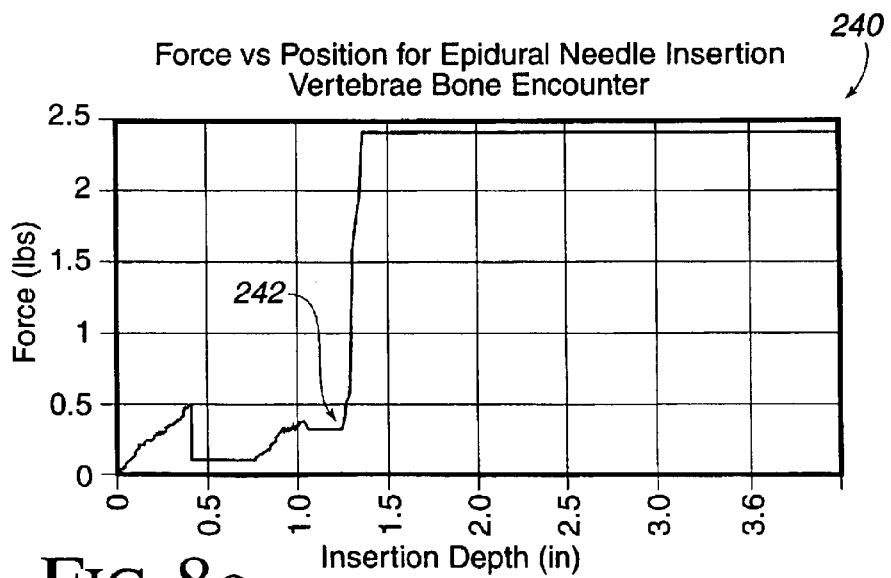

FIG. 8c is a graph 240 showing the force output on needle 18 from a physical property profile with respect to needle insertion depth in the simulated tissue for a "vertebrae bone encounter", i.e., an unsuccessful needle trajectory in an epidural anesthesia procedure. This profile is used when the needle is advancing through the simulated tissue. Assuming that the needle tip starts within the tissue, the force is fairly constant between 0 and about 1.25 inches to simulate the resistance of tissue of average stiffness on the needle (alternately, if the needle tip starts outside the tissue, an initial force spike similar to spile 232 can be provided to simulate puncturing of the skin). At point 242 (about 1.25 inches in the present example), a very large force spike (e.g., as large a force as can be generated) is output based on a very high (or infinite) stiffness stored in the profile to create a "virtual wall." This simulates a hard structure, such as bone, which the needle cannot advance through, and makes it apparent to the user that the needle must be retracted. The mechanical apparatus 25' is well-suited to simulated this bone encounter, since, to rapidly increase the output force without introducing vibrations or instabilities, several requirements must be met. These requirements include a mechanical stiffness high enough so that components do not deflect under the input load; a transmission free of backlash and deflection under the force load; and a position resolution high enough that the discrete changes in force output do not cause vibrations in the linear axis. In the preferred embodiment of apparatus 25', the apparatus 25' is able to simulate a bone tissue stiffness of approximately 20 lbs/in., which is more than sufficient to simulate a bone encounter in the procedure.

Once a bone encounter is apparent, the user can retract the needle to just below the skin surface, shift the angular position of the needle, and try advancing the needle again. If the user believes that the needle almost missed the bone, then the needle can be retracted slightly and continued to be advanced while exerting a sideward force on the needle to move it away from the bone. Simulated tissue resistance and compliance can be important to realistically simulate these multiple forces on the needle, as well as forces about axes A and B provided by actuators 86a and 86b.

Referring back to FIG. 8, after step 218, the process continues to step 220. In step 220, the process calculates the force to output to the actuators based on appropriate parameters, such as the current position and/or previous position(s) of the needle in the simulated tissue and based on a value in the selected physical property profile that corresponds to the current position of the tip of the needle. The calculation of the force value is influenced by needle movement and parameters such as compliance and resistance of the tissue (which can also be stored in the profiles). In alternate embodiments, the calculated force value can be dependent on more complex factors. For example, the stiffness of the tissue at the tip of the needle as well as the stiffness of tissue on the sides of shaft 28 can be taken into account when calculating the force. In such an embodiment, the physical properties at different depths can be retrieved from the profile for different portions of the needle. In addition, the size (width/length) of needle 18 and the type of needle 18 (e.g., shape, material, etc.) can be used to influence the calculation of the force output on user object 44.

The computer then outputs the calculated force value(s) to the actuator interface that includes DAC 154 and power amplifier 156, and the appropriate forces are generated on needle 18 (or other object 44) by actuators 86a, 86b, and 86c. In addition, if the epidural space has been reached by the needle 18 in a successful needle trajectory, then the valve 89 is preferably opened so that the plunger 27 has no pressure exerted on it and can be moved by the user to simulate the "loss of resistance" in an epidural procedure. The valve, 89 is also opened if the needle is not contacting any tissue (the valve 89 is closed at all other times to provide pressure on the plunger 27 while the needle is within other tissue). The process then returns to step 206 to retrieve updated sensor data from the sensors, and the process continues as described above.

Figure 9:
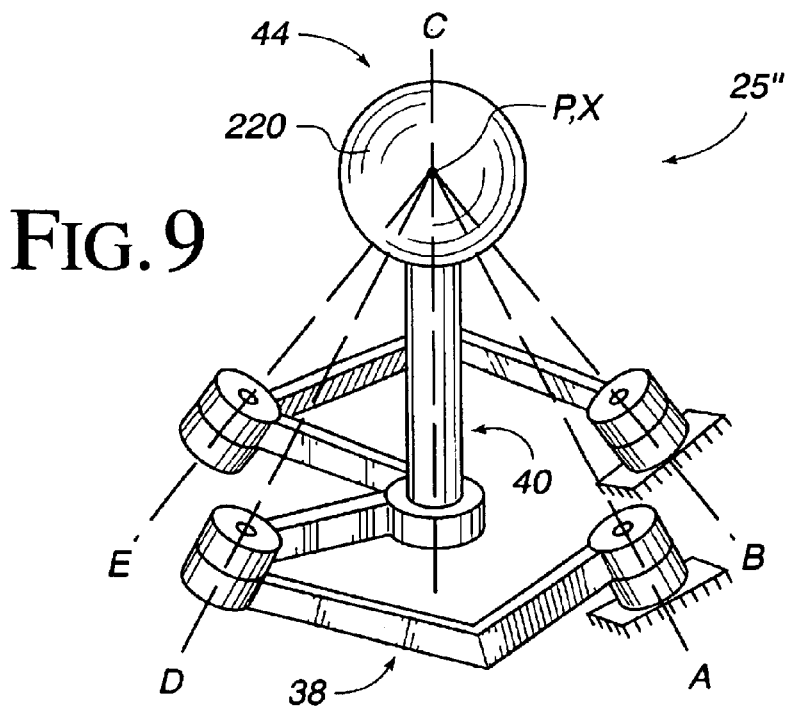
FIG. 9 is a diagrammatic view of an alternate embodiment of the gimbal apparatus of FIG. 2a including a spherical user manipulatable object.

FIG. 9 is a schematic diagram of an alternate embodiment 25" of mechanical apparatus 25 for use with a spherical user object or joystick user object. Apparatus 25 includes a gimbal mechanism 38 and a linear axis member 40 similar to the mechanisms 38 and 40 described above with reference to FIG. 2a. Linear axis member 40 is preferably a cylindrical or other shaped shaft. In FIG. 9, user manipulatable object 44 is a spherical ball 220 whose center X is positioned at or close to remote pivot point P at the intersection of axes A, B, D, and E. A user can grasp ball 220 and rotate the ball about pivot point P in two degrees of freedom about axes A and B. In the preferred embodiment, ball 220 cannot be moved in a linear degree of freedom since it is desired to keep ball 220 centered at point P. Alternatively, such a linear third degree of freedom can be implemented as described in embodiments above.

Since the remote pivot point P is at the center of ball 220, the ball will seem to rotate in place when it is moved in the provided degrees of freedom. This unique motion allows a user to fully grasp the rotating object, such as ball 220, without having a large support structure interfering with the user's grasp.

Additionally, a third rotary degree of freedom can be added for ball 220 as rotation or "spin" about axis C extending through the pivot point P and aligned with linear axis member 40. This third degree of freedom allows ball 220 to spin in place about its center.

As in the above embodiments, sensors and actuators can be included in apparatus 25" to provide an interface with a computer system The sensors provide information about the position of the object in one, two, and/or three degrees of freedom to the computer system, and the actuators are controlled by the computer system to output forces in one or more degrees of freedom. Some desired applications for apparatus 25" include a controller to manipulate the movement of computer-displayed images for CAD systems, video games, animations, or simulations and to provide forces to the user when the controlled images interact with other images or when otherwise appropriate. For example, the ball 220 can be rotated in different degrees of freedom to steer a vehicle through a computer-simulated environment. Also, apparatus 25" can be used to remotely control real objects (teleoperation), such as remotely steering a real vehicle.

In alternate embodiments, ball 220 can include protrusions and/or indentations which conform to a user's hand and allow the user to grip the ball 220 more securely. Or, other-shaped objects 44 can be provided, such as a cylinder, ellipsoid, grip, etc., centered at point P. In yet other embodiments, linear axis member 40 can be extended so that pivot point P is positioned at a point on the liear axis member. The ball 220 could then be moved in two rotary degrees of freedom about pivot point P like a conventional joystick device.

Figure 9A:
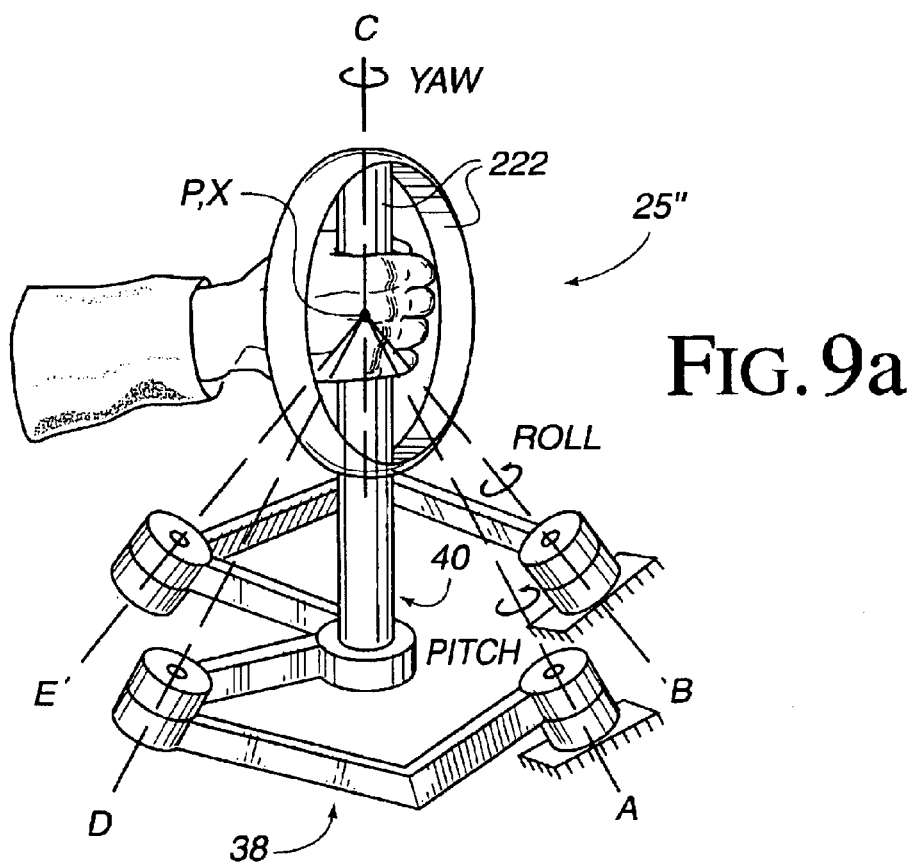
FIG. 9a is a diagrammatic view of an alternate embodiment of the mechanical apparatus and user manipulatable object of FIG. 9.

FIG. 9a is a perspective view of an alternate embodiment of the mechanical apparatus and user object of FIG. 9. In FIG. 9a, user manipulatable object 44 is a handle grip 222, where the the center X of the grip is approximately positioned at the remote pivot point P. A user can grasp the grip 222 as shown. Preferably, three degrees of freedom about axes A, B, and C are provided as described above. Grip 222 is suitable for embodiments implementing video games or simulations.

One useful application for mechanical apparatus 25" with grip 222 is for controlling computer-generated objects in a simulation (including video games) implemented by computer 16 and which can be displayed on computer screen 20 as graphical objects. In a "position control" paradigm between interface apparatus 25" and the computer-generated object(s), movements of the grip 222 in provided degrees of freedom directly correspond to proportional movements of the controlled computer object such that locations in the workspace of the user object correspond directly to locations in the simulated space of the computer object. For example, moving grip 222 about axis C to a new position would move a displayed, controlled graphical cube about an equivalent axis on the display or move a cursor across the screen to an equivalent position on the display. In a "rate control" or "heading control" paradigm, movements of the grip 222 in provided degrees of freedom correspond to movements of the computer object in correponding directions or velocities to the grip movements. Rate control is often used to manipulate the velocity of a simulated controlled object, while heading control is used to manipulate the orientation of a displayed view/simulated entity, typically from a first person perspective. For example, using heading control, moving grip 222 about axis C would correspondingly move the view of a display screen and/or would move the cockpit of an aircraft in a simulated environment as if the user were in the cockpit. In some heading control embodiments, the three degrees of freedom can correspond to roll, pitch, and yaw controls mapped to the computer object in the simulation, as shown in FIG. 9a, where rotation about axes A and B is pitch and roll, and rotaton about axis C is yaw. Thus, the roll, pitch, and yaw of a simulated object, such as a vehicle (e.g., aircraft, spaceship, etc.), can be controlled using interface apparatus 25".

While this invention has been described in terms of several preferred embodiments, it is contemplated that alterations, modifications and permutations thereof will become apparent to those skilled in the art upon a reading of the specification and study of the drawings. For example, the apparatus 25 can be used for a variety of applications besides medical simulation, including vehicle simulation, video games, etc. Likewise, other types of gimbal mechanisms or different mechanisms providing multiple degrees of freedom can be used with the capstan band drive mechanisms disclosed herein to reduce inertia, friction, and backlash in a force feedback system. A variety of devices can also be used to sense the position of an object in the provided degrees of freedom and to drive the object along those degrees of freedom. Furthermore, certain terminology has been used for the purposes of descriptive clarity, and not to limit the present invention. It is therefore intended that the following appended claims include all such alterations, modifications and permutations as fall within the true spirit and scope of the present invention.

APPENDIX A

```
// EPIDURAL.CCP-- control software
#include <stdio.h>
#include <stdlib.h>
#include <math.h>
#include <dos.h>
#include <conio.h>
#include <time.h>
#include <iostream.h>
#include <graphics.h>
#include "forcio.h"    // forcio.h and other routines available from Immersion Corporation for interfacing
                      lower level functions, timing, etc. with a personal computer I/O card. Includes
                      function calls necessary to perform digital I/O, D/A output, encoder readings,
                      A/D conversions, etc.
#define rad(x) (M_PI/180*x)    //degrees to radians conversion
#define deg(x) (180/M_PI*x)    //radians to degrees conversion
#define BitsPerInchPound       1660   //(Bits per volt)*(volts per amp)*(Inch Pounds per amp)
```

-continued

APPENDIX A

```
#define MotorZeroOffset      2075    // Dac output = 0 volts
#define TRUE1
#define FALSE0
#define Airdepth     .5              //Distance along the linear axis before the skin is hit
//number of encoder counts per revolution
#define EncCount0    2000
#define EncCount1    2000
#define EncCount2    2000
// gear ratios
#define ReductionRatio0  1/(M_PI*.5)    // in/rev
#define ReductionRatio1  14    // rev of the link/rev of the motor
#define ReductionRatio2  14    // rev of the link/rev of the motor
// Axis initial positions
#define qInit0    0
#define qInit1    rad(70.50749)  // L1 = 70.50749
#define qInit2    rad(70.50749)  // L2 = 70.50749
// Link masses
#define mL1    .12124  // lbs
#define mL2    .08554  // lbs
#define mL3    .61158  //.10355lbs without linear axis
#define mL4    .11951  // lbs
// Positions of centers of mass of each link with respect to ground from Pro/E
#define GPL1C0i   -3.4166136
#define GPL1C1i   -.57972769
#define GPL1C2i   -3.6375004
#define GPL2C0i   -.91648391
#define GPL2C1i   .91648394
#define GPL2C2i   -4.0090091
#define GPL3C0i   .019861093    //.75034831 without linear axis installed*/
#define GPL3C1i   -.83162973    //.72411278 without linear axis installed*/
#define GPL3C2i   -5.5056730    //-4.3687943 without linear axis installed*/
#define GPL4C0i   3.4108646
#define GPL4C1i   -.57850482
#define GPL4C2i   -3.6279608
#define Advancing0
#define Retreating1
#define AdvancingRamp2
#define RetreatingRamp3
char ch;
int SkinBrokenFlag=FALSE, NeedleMode, done=0;
struct timeval Time;
long EncZero[3];
float interpolated_advance,interpolated_retreat;
float position_gain=120.0, force_gain=1.0/8000.0;
float OldSkinDepth=0,SkinDepth=0,NeedleDepth,TissueDeflection=.1,
    JointPositionAtPuncture[3]={0, rad(67.45845),rad(67.45845)};
float k, F[3], T[3], JointPosition[3], dJointPosition[3], ddJointPosition[3], G[3], TTissue[3];
float AmplifierCorrection[]={1.0, 1, 1}, BandCompensationOffset=.022,BandCompensationScalar=.022;
float InitialTorque[]={0.03,3.0,3.0},FinalTorque[3]={-.004,1.55,1.5};
float AngularTissueStiffness=50.0;
//working variables to find the positions of joint 2, 3, and 4 based on the positions of joint 1 and joint 5
double b,c,g,h,i,L[6],GP[3],phi,psi,phiAtPuncture,psiAtPuncture;
double V,dVdh,dVdg,dVdi,dVdL3,dVdL1,dVdL5,U,dUdb,dUdc,dUdL3,dUdL1,dUdL5;
//partial diiferentials of each z vector with respect to movement about the z vector of L1 and L5
double dL4dL1,dL4dL5,dL3dL1,dL3dL5,dL2dL1,dL2dL5;   //center of gravity vectors with respect to ground
double GPL1Ci[3],GPLCi[3],GPL3Ci[3],GPL4Ci[3];
//center of gravity vectors with respect to each links coordinate system
double L1PL1C[3],L2PL2C[3],L3PL3C[3],L4PL4C[3];
FILE *write_file_ptr;
// SkinDepth : needle submergence depth in skin
// NeedleDepth : distance from the non-deflected skin surface
// TissueDeflection : deflection of the the tissue that the needle is submerged in has been deflected
void control_loop();
void BoneProfile();
void OnTargetProfile();
void OutputMotorTorques();
void GetPos(void);
void GetEncZero();
void IntroText();
void Linear();
void Angular();
void CalcPosition();
void CalcGravityComp();
void CalcMotorTorques();
void CalcTTissue();
void CalcState();
void HandleMessage();
double CalcTime();
```

-continued

APPENDIX A

```
//////////////////////////////////////////////////
// void main(void)
//    This is program written to control a 1 DOF epidural
//    anesthesia simulator. Main enables the hardware and
//    the ability to insert menu options to try variety of
//    simulations. When the user quits, Main sets the motor
//    current to zero.
//////////////////////////////////////////////////
void main(void)
{
// --- Declaration ---
    int i=0;
// initialize the probe
    enable_dac();
    enable_enc();
    GetEncZero();
// open data file
    write_file_ptr=fopen("data2","w");
// initialize center of mass arrays with values from Pro/E
    GPL1Ci[0]=GPL1C0i;
    GPL1Ci[1]=GPL1C1i;
    GPL1Ci[2]=GPL1C2i;
    GPL2Ci[0]=GPL2C0i;
    GPL2Ci[1]=GPL2C1i;
    GPL2Ci[2]=GPL2C2i;
    GPL3Ci[0]=GPL3C0i;
    GPL3Ci[1]=GPL3C1i;
    GPL3Ci[2]=GPL3C2i;
    GPL4Ci[0]=GPL4C0i;
    GPL4Ci[1]=GPL4C1i;
    GPL4Ci[2]=GPL4C2i;
//vector from link 1's coordinate system to center of mass of link 1
    L1PL1C[0]=(.7301728566*GPL1Ci[0]-.19565351335*GPL1Ci[1].654655342*GPL1Ci[2]);
    L1PL1C[1]=(.3030677254*GPLiCi[0]-.765974189*GPL1Ci[1]+.566949392*GPL1Ci[2]);
    L1PL1C[2]=(-.61 23769025*GPL1Ci[0]-.612372205*GPL1Ci[1].5*GPL1Ci[2]);
//vector from link 2's coordinate system to center of mass of link 2
    L2PL2C[0]=(-.7071*GPL2Ci[0]-.7071*GP12Ci[1]+0*GPL2Ci[2]);
    L2PL2C[1]=(-.5*GPL2Ci[0]+.5*GPL2Ci[1]+.7071*GPL2Ci[2]);
    L2PL2C[2]=(-.5*GPL2Ci[0]+.5*GPL2Ci[1]+.7071*GPL2Ci[2]);
//vector from link 3's coordinate system to center of mass of link 3
    L3PL3C[0]=(.7071*GPL3Ci[0]-.7071*GPL3Ci[1]+0*GPL3Ci[2]);
    L3PL3C[1]=(-.7071*GPL3Ci[0]-.7071*GPL3Ci[1]+0*GPL3Ci[2]);
    L3PL3C[2]=(0*GPL3Ci[0]-1.4084988*GPL3Ci[1]-1*GPL3Ci[2]);
//vector from link 4's coordinate system to center of mass of link 4
    L4PL4C[0]=(-.73017*GPL4Ci[0]-.195649*GPL4Ci[1]-.65465*GPL4Ci[2]);
    L4PL4C[1]=(-.46567*GPL4Ci[0]+.843626*GPL4Ci[1]+.267258*GPL4Ci[2]);
    L4PL4C[2]=(.5*GPL4Ci[0]+.5*GPL4Ci[1 ]-.7071*GPL4Ci[2]);
// main control loop
    while (done)
        {
        // print instructions
        cout << "\n\n\n";
        cout << "";
        cout << "Press 1 to begin.\";
        cout << "\n";
        cout << "\n";
        cout << "Press Q to Quit.\n";
        // look for input from keyboard
        while(!kbhit()){}
        ch=getch();
        switch(ch)
        {
            case '1':   // Start
            case '1':
                cout << "   The Simulation has begun.\n";
                cout << "Please advance the needle at your leisure.\n";
                control_loop();
                break;
            case 'Q':   // Quit
            case 'q':
                done = 1;
                break;
            default:
                break;
        }
    }
// Set torques to final values for gentle resting of mechanism
    for (i=0;i<3;i++)
```

-continued

APPENDIX A

```
            T[i]=FinalTorque[i];
            OutputMotorTorques();
}
////////////////////////////////////////////////////////
// void control_loop()
// This function is the loop that runs while the simulator
// is operational. It obtains control from Main,
// calls GetPos to obtain the encoder position,
// calls CalcState to get the encoder position,
// calls OutputMotorTorques to send the desired force to the motors.
////////////////////////////////////////////////////////
void control_loop()
{
        int i=0;
        while (!done)
        {
            GetPos();
            CalcState();
            Angular();
            Linear();
            CalcMotorTorques();
            OutputMotorTorques();
            if (fmod(i,50)==0)
                HandleMessage();
            OldSkinDepth=SkinDepth;
        }
        done=0;
        cout << "   The Simulation has ended.\n";
        cout << "   We hope you enjoyed it.\n";
}
////////////////////////////////////////////////////////
// void Angular()
////////////////////////////////////////////////////////
void Angular()
{
    CalcPosition();
    CalcGravityComp();
    CalcTTissue();
}
////////////////////////////////////////////////////////
// void Linear()
////////////////////////////////////////////////////////
void Linear()
{
    if (((phiAtPuncture>rad(12.5))II(phiAtPuncture<rad(7.5)))II(psiAtPuncture>rad(3))II(psiAtPuncture<rad(-3))))
        BoneProfile();
        else
        OnTargetProfile();
}
////////////////////////////////////////////////////////
// void CalcMotorTorques()
////////////////////////////////////////////////////////
void CalcMotorTorques()
{
    switch(NeedleMode)
        {
        case Advancing:
            T[0]=interpolated_advance;
            break;
        case Retreating:
            T[0]=-interpolated_retreat;
            break;
        case AdvancingRamp:
            T[0]=((NeedleDepth-SkinDepth)/TissueDeflection)*interpolated_advance;
            break;
        case RetreatingRamp:
            T[0]=((NeedleDepth-SkinDepth)/TissueDeflection)*interpolated_retreat;
            break;
        }
    T[0]=T[0]+(BandCompensationOffset-BandCompensationScalar*JointPosition[0]);
    T[1]=G[1]+TTissue[1];
    T[2]=G[2]+TTissue[2];
}
////////////////////////////////////////////////////////
// void OutputMotorTorques()
// This function tales the output from CalcMotorTorques, coverts it to the correct units and
// outputs it to the correct channel
////////////////////////////////////////////////////////
```

-continued

APPENDIX A

```
void OutputMotorTorques()
{
    int i;
    float output ReductionRatio[3], Direction[3],temp;
    ReductionRatio[0]=ReductionRatio0;
    ReductionRatio[1]=ReductionRatio1;
    ReductionRatio[2]=ReductionRatio2;
    Direction[0]=1;
    Direction[1]=1;
    Direction[2]=1;
    for (i=0;i<3;i++)
    {
        output=MotorZeroOffset+(T[i]*AmplifierCorrection[i]*BitsPerInchPound*Direction[i]/ReductionRatio[i]);
        if (output >= 4095) output = 4095;
        if (output <= 0) output = 0
        dac out(i, (unsigned)(output));
        if (i==0) temp=output;
    }
}
//////////////////////////////////////////////////////
// float GetPos(void)
//   This function is used by the control_loop to aquire the
//   encoder position
//////////////////////////////////////////////////////
void Getpos(void)
{
    long EncPos[3], ZerodEncPos[3];
    int EncCount[3], i=0;
    float ReductionRatio[3],qInit[3],Direction[3];
    EncCount[0]=EncCount0;
    EncCount[1]=EncCount1;
    EncCount[2]=EncCount2;
    ReductionRatio[0]=ReductionRatio0;
    ReductionRatio[1]=ReductionRatio1/(2*M_PI);
    ReductionRatio[2]=ReductionRatio2/(2*M_PI);
    qInit[0]=qInit0;
    qInit[1]=qInit1;
    qInit[2]=qInit2;
    Direction[0]=-1;
    Direction[1]=-1;
    Direction[2]=1;
    for (i=0;i<3;i++)
    {
        EncPos[i] = enc_n(i);
        ZerodEncPos[i] = EncPos[i]-EncZero[i];
        JointPosition[i] = ZerodEncPos[i]/(Direction[i]*EncCount[i]*ReductionRatio[i])+qInit[i];
    }
}
//////////////////////////////////////////////////////
// void GetEncZero()
// This function zeros the encoder position.
//////////////////////////////////////////////////////
void GetEncZero()
{
    int i;
    for (i=0;i<3;i++)
    {
        T[i] = InitialTorque[i];
    }
    OutputMotorTorques();
    cout << "   PLEASE PLACE THE MECHANISM ON THE\n";
    cout << "   CALIBRATION STAND AND PRESS ANY KEY\n";
    while (!kbhit()){}
    for (i=0;i<3;i++)
    {
        EncZero[i] = enc_in(i);
    }
}
//////////////////////////////////////////////////////
// void IntroText()
//////////////////////////////////////////////////////
void IntroText()
{
    cout << "   THE EPIDURAL ANESTHESIA SIMULATOR\n";
}
//////////////////////////////////////////////////////
// double CalcTime()
//////////////////////////////////////////////////////
```

-continued

APPENDIX A

```
double CalcTime()
{
    double CTime;
    hd_gettimeofday(&Time);
    CTime=double(Time.tv_sec)+double(Time.tv_usec)1000000.0;
    return(CTime);
}
//////////////////////////////////////////////////////////
// void CalcTissue()
// This function calculates the angular positioning of the needle as it breaks
// skin and the torque exerted by the tissue due to angular movement of the
// needle after the skin is punctured. This function also enables changes in
// the trajectory of the needle based on needle advancement while angular torque
// is being exerted on the needle by the user.
//////////////////////////////////////////////////////////
void CalcTTissue()
{
    if (SkinDepth>0)
    {
        if (SkinBrokenFlag==FALSE)
        {
        // Set initial needle trajectory as skin is broken
            JointPositionAtPuncture[1]=JointPosition[1];
            JointPositionAtPuncture[2]=JointPosition[2];
            phiAtPuncture=phi;
            psiAtPuncture=psi;
            SkinBrokenFlag=TRUE;
        }
        if (SkinDepth>OldSkinDepth)
        {
        // Modify trajectory of the needle due to advancement with torque being applied
            JointPositionAtPuncture[1]=(JointPositionAtPuncture[1]+.005/SkinDepth*JointPosition[1])/(1+
                .005/SkinDepth);
            JointPositionAtPuncture[2]=(JointPositionAtPuncture[2]+.005/SkinDepth*JointPosition[2])/(1+
                .005/SkinDepth);
            phiAtPuncture=(phiAtPuncture+.005/SkinDepth*phi)/(1+.005/SkinDepth);
            psiAtPuncture=(psiAtPuncture+.005/SkinDepth*psi)/(1+.005/SkinDepth);
        }
// calculate torque applied on the needle by the tissue.
        TTissue[1]=AngularTissueStiffness*(JointPosition[1]-JointPositionAtPuncture[1])*SkinDepth*SkinDepth;
        TTissue[2]=AngularTissueStiffness*(JointPosition[2]-JointPositionAtPuncture[2])*SkinDepth*SkinDepth;
    }
    if (SkinDepth<=TissueDeflection)
    {
        SkinBrokenFlag=FALSE;
        TTissue[1]=0;
        TTissue[2]=0;
    }
}
//////////////////////////////////////////////////////////
// void CalcState()
// This function determines the current state of the needle
//////////////////////////////////////////////////////////
void CalcState()
{
    NeedleDepth = JointPosition[0]-AirDepth;
    k = SkinDepth*position_gain;
    if ((NeedleDepth-TissueDeflection)>=SkinDepth)
    {
        NeedleMode=Advancing;
        SkinDepth=NeedleDepth-TissueDeflection;
    }
    else if ((NeedleDepth+TissueDeflection)<=SkinDepth)
    {
        NeedleMode=Retreating;
        SkinDepth=NeedleDepth+TissueDeflection;
    }
    else if (NeedleDepth>SkinDepth)
    {
        NeedleMode=AdvancingRamp;
    }
    else if (NeedleDepth<SkinDepth)
    {
        NeedleMode=RetreatingRamp;
    }
}
void HandleMessage()
// This function takes input from the keyboard and performs the
```

-continued

APPENDIX A

```
// appropriate function
//////////////////////////////////////////////////
void HandleMessage()
{
    int i;
    if(kbhit())
    {
        ch=getch();
        switch(ch)
        {
            case 'Q':
            case 'q':
                done = 1;
                for (i=0;i<3;i++)
                    T[i]=InitialTorque[i];
                OutputMotorTorques();
                break;
            case 'm':
                AmplifierCorrection[1]=AmplifierCorrection[1]+.01;
                cout << "AmplifierCorrection[1] = " << AmplifierCorrection[1] << "\n"endl;
                break;
            case 'n':
                AmpiifierCorrection[1]=AmplifierCorrection[1]-.01;
                cout << "AmplifierCorrection[1] = "AmplifierCorrection[1] <<"\n" <<endl;
                break;
            case '.':
                AmplifierCorrection[2]=AmplifierCorrection[2]+.01;
                cout << "AmplifierCorrection[2] = " <<AmplifierCorrection[2] << " ϑ n" << endl;
                break;
            case ',':
                AmplifierCorrection[2]=AmplifierCorrection[2]-.01;
                cout << "AmplifierCorrection[2] = " << AmplifierCorrection[2] << "n\" << endl;
                break;
            case 'b':
                AngularTissueStiffness=AngularTissueStiffness+1;
                cout << "AngularTissueStiffness = " << AngularTissueStiffness << "\n" << endl;
                break;
            case 'v':
                AngularTissueStiffness=AngularTissueStiffness-1;
                cout << "AngularTissueStiffness = " AngularTissueStiffness << "\n" <<endl;
                break;
            case 's':
                BandCompensationScalar=BandCompensationScalar+.001;
                cout << "BandCompensationScalar = " BandCompensationScalar << "\n" <<endl;
                break;
            case 'a':
                BandCompensationScalar=BandCompensationScalar-.001;
                cout << "BandCompensationScalar = " << BandCompensationScalar << "\n" << endl;
                break;
            case 'f':
                BandCompensationOffset=BandCompensationOffset+.001;
                cout << "BandCompensationScalarOffset = " << BandCompensationOffset << "\n" << endl;
                break;
            case 'd':
                BandCompensationOffset=BandCompensationOffset-.001;
                cout << "BandCompensationScalarOffset = " << BandCompensationOffset << "\n" << endl;
                break;
            case 'g':
                printf("G = %f %f \n",G[1],G[2]);
                break;
            default:
                break;
        }
    }
}
//////////////////////////////////////////////////
// void OnTargetProfile()
//   This function contains the force profile for a successful trajectory
//////////////////////////////////////////////////
void OnTargetProfile()
{
// Force profile modified for a less ridid Ligamentum Flavum and a shorter
// subcutaneous fat layer then modified to add texture
    static float advance_data[400] =
    {
20,60,100,140,180,220,260,300,335,366,387,406,426,446,465,486,
506,527,548,570,591,613,635,657,680,703,740,780,820,860,900,210,
220,220,220,220,220,220,220,220,220,220,220,220,220,220,220,220,
```

-continued

APPENDIX A

```
220,220,220,220,220,220,220,220,220,220,220,240,260,280,300,320,
340,390,420,470,500,550,620,550,610,570,630,590,570,650,700,700,
700,600,620,600,700,600,600.500,600,600,600,700.700,700,600,600,
600,700,600,500,500,700,600,600,600,500,500,600,500,600,600,
600,600,600,600,600,600,600,600,600,600,600,600,600,600,600,600,
700,600,600,500,500,600,500,700,600,600,600,600,600,600,600,
600,600,600,600,600,600,600,600,600,600,600,600,600,600,600,600,
600,600,600,700,600,600,500,600,600,500,600,700,600,600,700,600,
600,600,600,600,600,600,600,600,700,600,600,800,500,600,600,600,
600,600,700,700,800,700,600,600,500,600,600,600,600,600,600,600,
600,600,800,800,800,600,700 700,800,700,800,800,800,800,900,900,
500,500,500,500,500,500,500,500,500,500,500,500,500,500,500,500,
500,500,500,500,500,500,500,500,500,500,500,500,500,500,500,500,
500,500,500,500,500,500,500,500,500,500,500,500,500,500,500,500,
500,500,500,500,500,500,500,500,500,500,500,500,500,500,500,500,
500,500,500,500,500,500,500,500,500,500,500,500,500,500,500,500);
/*(0,6,12,18,26,35,44,54,65,76,88,100,112,126,139,153,165,183,197,
213,229,245,262,279,296,314,332,350,368,387,406,426,446,465,486,
506,527,548,570,591,613,635,657,650,703,740,780,820,560,900,210,
220,220 220,220,220,220,220,220,220,220,220,220,220,220,220,220,
220,220,220,220,220,220,220,220,220,220,220,240,260,280,300,320,
340,390,420,470,500,550,620,550,610,570,630,590,570,650,700,700,
700,600,600,600,600,600,600,600,600,600,600,600,600,600,600,600,
600,600,600,600,600,600,600,600,600,600,600,600,600,600,600,600,
600,600,600,600,600,600,600,600,600 600,600,600,600,600,600,600,
600,600,600,600,600,600,600,600,700,600,600,600,600,600,600,600,
600,600,600,600,600,600,600,600,600,600,600,600,600,600,600,600,
600,600,600,600,600,600,600,600,600,600,600,600,600,600,700,600,
600,600,600,600,600,600,600,600,700,600,600,600,600,600,600,600,
600,600,600,600,600,600,600,600,600,600,600,600,600,600,600,600,
600,600,600,600,600,600,600,600,600,600,600,600,600,600,600,600,
100,100,100,100,100,100,100,100,100,100,100,100,100,100,100,100,
100,100,100,100,100,100,100,100,100,100,100,100,100,100,100,100,
100,100,100,100,100,100,100,100,100,100,100,100,100,100,100,100,
100,100,100,100,100,100,100,100,100,100,100,100,100,100,100,100,
100,100,100,100,100,100,100,100,100,100,100,100,100,100,100);
*/
// retreat force profile
    static float retreat_data[400] =
(0,2,4,6,8,10,12,14,16,18,20,22,24,26,28,30,32,34,36,38,40,42,44,46,48,50,52,54,56,58,60,62,
64,66,68,70,72,74,76,78,80,82,84,86,88,90,92,94,96,98,99,100,101,102,103,104,105,106,107,
108,109,110,111,112,113,114,115,116,117,118,119,120,121,122,123,124,125,126,127.5,129,130.5,
132,133.5,135,136.5,138,139.5,141,142.5,144,145.5,147,148.5.150,151.5,153,154.5,156,157,158,
182,183,184,185,186,187,188,189,190,191,192,193,194,195,196,197,198,199,200,201,202,203,204,
205,206,207,208,209,210,211,212,213,214,215,216,217,218,219,220,221,222,223,224,225,226,227,
228,229,230,231,232,233,234,235,236,237,238,239,240,241,242,243,244,245,246,247,248,249,250,
251,252,253,254,255,256,257,258,259,260,261,262,263,264,265,266,267,268,269,270,271,272,273,
274,275,276,277,278,279,280,281,287,293,299,305,311,317,323,329,335,341,347,353,359,365,371,
377,383,389,395,401,407,413,419,425,431,437,443,449,455,461,467,473,479,480,481,482,483,484,
485,486,487,488,489,490,491,500,500,500,500,500,500,500,500,500,500,500,500,500,500,500,500,500,500,
500,500,500,500,500,500,500,500,500,500,500,500,500,500,500,500,500,500,500,500,500,500,500,500,
500,500,500,500,500,500,500,500,500,500,500,500,500,500,500,500,500,500,500,500,500,500,500
500,500,500,500,500,500,500,500,500,500,500,500,500,500,500,500,500,500,500,500,500
500,500,500,500,500,500,500,500,500,500,500,500,500,500,500,500,500,500,500,500,500
500,500,500,500,500,500,500,500,500,500,500,500,500,500,500,500,500,500,500,500,500};
    int j;
    j = (int)k;
// open plunger valve if needle is out of skin or in epidural space
    if ((NeedleDepth-AirDepth <= 0)II(j>=208))
        dac_out(3, (unsigned)(2200)):
    else
        dac_out(3, (unsigned)(2073));
    if ((j >= 380)II(j<0))
    {
        interpolated_advance = 0;
        interpolated_retreat = 0;
    }
    else
    // calculate linear interpolation of force profile data
        interpolated_advance = (advance_data[j]+((k-(float)(j))*(advance_data[j+1]\
        -advance data[j])))*force_gain;
        interpolated_retreat = (retreat data[j]+((k-(float)(j))*(retreat_data[j+1]\
        -retreat_data[j])))*force_gain;
}
//////////////////////////////////////////////
// void BoneProfile()
//   This function contains the force profile for a bone encounter
//////////////////////////////////////////////
```

APPENDIX A

```
void BoneProfile()
{
// Educated estimation of what a bone encounter might be like
    static float advance_data[400] =
    {
20,60,100,140,180,220,260,300,335,368,387,406,426,446,465,486,
506,527,548,570,591,613,635,657,680,703,740,780,820,860,900,210,
220,220,220,220,220,220,220,220,220,220,220,220,220,220,220,220,
220,220,220,220,220,220,220,220,220,220,220,240,260,280,300,320,
340,390,420,470,500,550,620,550,610,570,630,590,570,650,700,700,
700,600,600,600,600,600,600,600,600,600,600,600,600,600,600,600,
700,900,1100,1700,2400,3000,3600,4000,4400,4400,4400,4400,4400,4400,
4400,4400,4400,4400,4400,4400,4400,4400,4400,4400,4400,4400,4400,4400,4400,4400,
4400,4400,4400,4400,4400,4400,4400,4400,4400,4400,4400,4400,4400,4400,4400,4400,
4400,4400,4400,4400,4400,4400,4400,4400,4400,4400,4400,4400,4400,4400,4400,4400,
4400,4400,4400,4400,4400,4400,4400,4400,4400,4400,4400,4400,4400,4400,4400,4400,
4400,4400,4400,4400,4400,4400,4400,4400,4400,4400,4400,4400,4400,4400,4400,4400,
4400,4400,4400,4400,4400,4400,4400,4400,4400,4400,4400,4400,4400,4400,4400,4400,
4400,4400,4400,4400,4400,4400,4400,4400,4400,4400,4400,4400,4400,4400,4400,4400,
4400,4400,4400,4400,4400,4400,4400,4400,4400,4400,4400,4400,4400,4400,4400,4400,
4400,4400,4400,4400,4400,4400,4400,4400,4400,4400,4400,4400,4400,4400,4400,4400,
4400,4400,4400,4400,4400,4400,4400,4400,4400,4400,4400,4400,4400,4400,4400,4400,
4400,4400,4400,4400,4400,4400,4400,4400,4400,4400,4400,4400,4400,4400,4400,4400};
// Estimation of what the retreat data for a bone encounter profile might feel like
    static float retreat_data[400] =
{0,2,4,6,8,10,12,14,16,18,20,22,24,26,28,30,32,34,36,38,40,42,44,46,48,50,52,54,56,58,60,62,
64,66,68,70,72,74,76,78,80,82,84,86,88,90,92,94,96,98,99,100,101,102,103,104,105,106,107,
108,109,110,111,112,113,114,115,116,117,118,119,120,121,122,123,124,125,126,127.5,129,130.5,
132,133.5,135,136.5,138,139.5,141,142.5,144,145.5,147,148.5,150,151.5,153,154.5,156,157,158,
159,160,161,162,163,164,165,166,167,168,169,170,171,172,173,174,175,176,177,178,179,180,181,
182,183,184,185,186,187,188,189,190,191,192,193,194,195,196,197,198,199,200,201,202,203,204,
205,206,207,208,209,210,211,212,213,214,215,216,217,218,219,220,221,222,223,224,225,226,227,
228,229,230,231,232,233,234,235,236,237,238,239,240,241,242,243,244,245,246,247,248,249,250,
251,252,253,254,255,256,257,258,259,260,261,262,263,264,265,266,267,268,269,270,271,272,273,
274,275,276,277,278,279,280,281,287,293,299,305,311,317,323,329,335,341,347,353,359,365,371,
377,383,389,395,401,407,413,419,425,431,437,443,449,455,461,467,473,479,480,481,482,483,484,
485,486,487,488,489,490,491,0,0,0,0,0,0,0,0,0,0,0,0,0,0,0,0,0,0,0,0,0,
0,0,0,0,0,0,0,0,0,0,0,0,0,0,0,0,0,0,0,0,0,0,0,0,0,0,0,0,0,0,0,
0,0,0,0,0,0,0,0,0,0,0,0,0,0,0,0,0,0,0,0,0,0,0,0,0,0,0,0,0,0,0,0,0,0,
0,0,0,0,0,0,0,0,0,0,0,0,0,0,0,0,0,0,0,0,0,0,0,0,0};
    int j;
    j = int(k;
// open plunger valve if the needle is outside of skin or in epidural space
    if (NeedleDepth-AirDepth <= 0)
        dac_out(3, (unsigned)(2200));
    else
        dac_out(3, (unsigned)(2073));
if ((j >= 380)ll(j<0))
    {
        interpolated_advance = 0;
        interpolated_retreat = 0;
    }
    else
    // calculate linear interpolation of force profile
        interpolated_advance = (advance_data[j]+((k-(float)(j))*(advance_data[j+1]\
        -advance_data[j])))*force_gain;
        interpolated_retreat = (retreat data[j]+((k-(float)[j))*(retreat_data[j+1]\
        -retreat_data[j])))*force gain;
}
/////////////////////////////////////////////////////
// void CalcPosition()
//   This function calculates the angular position of each link
/////////////////////////////////////////////////////
void CalcPosition()
}
    L[1]=JointPosition[1];
    L[5]=JointPosition[2];
    b = -cos(L[5])*sin(L[1])-.25*sin(L[5])*cos(L[1]);
    c = .96825*sin(L[5]);
    g = .93541*sin(L[5])*cos(L[1])+.2338525*cos(L[5])*sin(L[1])+.3423247875*sin(L[1]);
    h = -.93541*sin(L[5])*sin(L[1])+.2338525*cos(L[5])*cos(L[1])+.3423247875*cos(L[1]);
    i = -.9057107325*cos(L[5])+.0883875;
// Calculate joint angle of frame 3
    L[3]=-(1.57079+asin(-1-1.87080*h+.70710*i));
// Calculate joint angle of frame 4
    L[4]=2*atan(((.5)/(-32275e10*sin(L[3])+42695e10*b-16137e10*c))*
        (-45644e10*cos(L[3])-45644e10+sqrt(2.08339e29*cos(L[3])*cos(L[3])+
```

-continued

APPENDIX A

```
            4.16678e29*cos(L[3])+2.08339e29+4.16674e29'sin(L[3])'sin(L[3])-
            7.291 66e29*b*b+5.51195e29*b*c-1.04165e29*c*c)));
// Calculate joint angle of frame 2
      L[2]=2*atan(((.5)/(7.0711e4*sin(L[3])+10.0000e4*g))*(7.0710e4*h+1.87082e5*i+
            sqrt(50000e5*h*h+26457e6*h*i+34999e6*i*i-20000e6*sin(L[3])'sin(L[3])
            +40000e6*g*g)));
// Calculate the needle vector with respect to the ground coordinate system
      GP[0]=.5590199527*sin(L[5])*sin(L[4])-.197641504277085*cos(L[4])*cos(L[5])+
            .405044644214287*cos(L[4])-.522912853955107*cos(L[5])-.153091728719985;
      GP[1]=-.44721525505*sin(L[4])*cos(L[5])+.3354105574*sin(L[5])*sin(L[4])-
            .1581129534229275*sin(L[5])*cos(L[4])-.118584402568770*cos(L[4])*cos(L[5])-
            .405044644214287*cos(L[4])-.4183296217263205'sin(L[5])-.313746389497534*cos(L[5])+
            .153091728719985;
      GP[2]=.5477274060*sin(L[4])*cos(L[5])+.2738637030*sin(L[5])*sin(L[4])+
            .193649024391300*sin(L[5])*cos(L[4])-9.6824512195650e-2*cos(L[4])*cos(L[5])-
            .33071888255*cos(L[4])+.512349692846460'sin(L[5])-.256174846423230*cos(L[5])+
            .12499937025;
// Calculate the needle's orientation angles
phi=atan(GP[0]/GP[2]);
psi=atan(GP[1]/GP[2]);
}
/////////////////////////////////////////////////////////
// void CalcGravityComp()
//   This functlon calculates gravity compensation force output for the
// given mechanism position
/////////////////////////////////////////////////////////
void CalcGravityComp()
{
double dbdL1,dcdL1,dgdL1,dhdL1,didL1,dbdL5,dcdL5,dgdL5,dhdL5,didL5;
double dGPL1CdL1[3],dGPL1CdL5[3];
double dGPL2CdL1 [3],dGPL2CdL5[3],dGPL3CdL1[3],dGPL3CdL5[3],dGPL4CdL1[3],dGPL4CdL5[3];
double SingularityFlag, SingularityFlag2;
// Calculate Partial differential of L4 with respect to L1 and L5
dbdL1=cos(L[5])*cos(L[1])+.25*sin(L[5])*sin(L[1]);
dcdL1=0;
dgdL1=.93541*sin(L[5])*sin(L[1])+.23385*cos(L[5])*cos(L[1])+.34232*cos(L[1]);
dhdL1=.93541*sin(L[5])*cos(L[1])-.23385*cos(L[5])*sin(L[1])-.34232*sin(L[1]);
didL1=0;
dbdL5=sin(L[5])*sin(L[1])-.25*cos(L[5])*cos(L[1]);
dcdL5=96825*cos(L[5]);
dgdL5=93541*cos(L[5])*cos(L[1])-.23385*sin(L[5])*sin(L[1]);
dhdL5=.93541*cos(L[5])*sin(L[1])-.23385*sin(L[5])*cos(L[1]);
didL5=.90571*sin(L[5]);
// Remove Singularity
      SingularityFlag2=(70711.*sin(L[3])+100000.*g);
      if ((SingularityFlag2<2000)&&(SingularityFlag2>-900))
      {}
      else
      {
//Find partial differential of L2 with respect to L1 and L5
V=.5/(70711.*sin(L[3])+100000.*g)*(70710.*h+187082.*i+sqrt(.5e10*h*h+2.64571e10*h*i+
3.49996e10*i*i-2e10*sin(L[3])*sin(L[3])+4e10*g*g));
dVdg=-50000.0/pow((70711.*sin(L[3])+100000.*g),2)*(70710.*h+187082.*i+sqrt(.5e10*h*h+
2.64571e10*h*i+3.5e10*i*i-2e10*pow(sin(L[3]),2)+4e10*g*g))+2e10/(70711.*sin(L[3])+100000.*g)/
sqrt(.5e10*h*h+2.64571e10*h*i+3.5e10*i*i-2e10*sin(L[3])*sin(L[3])+4e10*g*g)*g;
dVdh=(.5/(70711.*sin(L[3])+100000.*g))*(70710.+(1/(2*sqrt(.5e10*h*h+2.64571e10*h*i+
3.5e10*i*i-2.0e410*sin(L[3])*sin(L[3])+4.0e10*g*g)))*(1e10*h+2.64571e10*i));
dVdi=(.5/(70711.*sin(L[3])+100000.*g))*(187082.+(1/(2*sqrt(.5e10*h*h+2.64571e10*h*i+
3.5e10*i*i-2e10*sin(L[3])*sin(L[3])+4e10*g*g)))*(2.64571 e10*h+7e10*i));
dVdL3=-35355.5/pow((70711.*sin(L[3])+100000.*g),2)*(70710.*h+187082.*i+
sqrt(.5e10*h*h+2.64571e10*h*i+3.5e10*i*i-2e10*sin(L[3])*sin(L[3])+4e10*g*g))*cos(L[3])-
1e10/(70711.*sin(L[3])+100000.*g)/sqrt(.5e10*h*h+2.64571 e10*h*i+3.5e10*i*i-
2e10*sin(L[3])*sin(L[3])+4e10*g*g)*sin(L[3])*cos(L[3]);
dL3dL1=(1.87080*dhdL1-.70709*didL1)/sqrt(1-(1+1.87080*h-.70709*i)*(1+1.87080*h-.70709*i));
dL3dL5=(1.87080*dhdL5-.70709*didL5)/sqrt(1-(1+1.87080*h-.70709*i)*(1+1.87080*h-.70709*i));
dVdL1=dVdL3*dL3dL1+dVdg*dgdL1+dVdh*dhdL1+dVdi*didL1;
dVdL5=dVdL3*dL3dL5+dVdg*dgdL5+dVdh*dhdL5+dVdi*didL5;
dL2dL1=(2/(1+V*V))*dVdL1;
dL2dL5=(2/(1+V*V))*dVdL5;
}
// Remove Singularity
      SingularityFlag=(-3.22752e14*sin(L[3])+4.26956e14*b-1.61373e14*c);
      if ((SingularityFlag<3e12)&&(SingularityFlag>-2.5e12)){}
      else
      {
// Find partial difterential of L4 with respect to L1 and L5
U=.5/(-3.22752e14*sin(L[3])+4.26956e14*b-1.61373e14*c)*(-45644e10*cos(L[3])-
45644e10+sqrt(2.08339e29*cos(L[3])*cos(L[3])+4.16678e29*cos(L[3])+2.08339e29+
```

-continued

APPENDIX A

```
4.16674e29*sin(L[3])*sin(L[3])-7.29167e29*b*b+5.511957e29*b*c-1.04165e29*c*c));
dUdb=(-2.13478e14/(pow((-3.22752e14*sin(L[3])+4.26956e14*b-1.61373e14*c),2)))*
(-4.56441e14*cos(L[3])-4.56442e14+sqrt(2.08339e29*cos(L[3])*cos(L[3])+4.16678e29*cos(L[3])+
2.08339e29+4.16674e29*sin(L[3])*sin(L[3])-7.29166e29*b*b+5.51195e29*b*c-1.04165e29*c*c))+
((.25*(-1.45833e30*b+5.51195e29*c))/((-3.22752e14*sin(L[3])+4.26956e14*b-1.61373e14*c)*
sqrt(2.08339e29*cos(L[3])*cos(L[3])+4.16678e29*cos(L[3])+2.08339e29+4.166745e29*sin(L[3])*
sin(L[3])-7.29167e29*b*b+5.51195e29*b*c-1.04165e29*c*c)));
dUdc=(8.06867e13/(pow((-3.22752e14*sin(L[3])+4.26956e14*b-1.61373e14*c),2))*
(-4.56441e14*cos(L[3])-4.56442e14+sqrt(2.08339e29*cos(L[3])*cos(L[3])+4.16678e29*cos(L[3])+
2.08339e29+4.16674e29*sin(L[3])*sin(L[3])-7.29166e29*b*b+5.51195e29*b*c-1.04165e29*c*c))
+.25/(-3.22752e14*sin(L[3])+4.26956e14*b-1.61373e14*c)/sqrt(2.08339e29*cos(L[3))*cos(L[3])+
4.16678e29*cos(L[3])+2.08339e29+4.166745e29*sin(L[3])*sin(L[3])-7.29167e29*b*b+5.51195e29*b*c-
1.04165e29*c*c)*(5.51195e29*b-2.08331e29*c));
dUdL3=1.61375e14/pow((-3.22752e14*sin(L[3])+4.26956e14*b-1.61373e14*c),2)*
(-4.56441e14*cos(L[3])-4.56442e14+sqrt(2.08339e29*cos(L[3])*cos(L[3])+4.16878e29*cos(L[3])+
2.08339e29+4.16674e29*sin(L[3])*sin(L[3])-7.29166e29*b*b+5.51195e29*b*c-1.04165e29*c*c))*cos(L[3])+
5/((-3.22752e14*sin(L[3])+4.26956e14*b-1.61373e14*c))*(4.56442e14*sin(L[3])+
(.5*(4.16670e29*cos(L[3])*sin(L[3])-4.16678e29*sin(L[3])))/
sqrt(2.08339e29*cos(L[3])*cos(L[3])+4.16678e29*cos(L[3])+2.08339e29+
4.166745e29*sin(L[3])*sin(L[3])-7.29167e29*b*b+5.51195e29*b*c-1.04165e29*c*c));
dUdL1=dUdL3*dL3dL1+dUdb*dbdL1+dUdc*dcdL1;
dUdL5=dUdL3*dL3dL5+dUdb*dbdL5+dUdc*dcdL5;
dL4dL1=(2/(1+U*U))*dUdL1;
dL4dL5=(2/(1+U*U))*dUdL5;
}
// Find partial differentials of the center of gravity vectors of each link
//with respect to L1 and L5
dGPL1CdL1[1]=(-.632455*sin(L[1])*L1PL1C[0]-.4743422525*cos(L[1])*L1PL1C[0]-
.632455*cos(L[1])*L1PL1C[1]+.4743422525*sin(L[1])*L1PL1C[1]);
dGPL1CdL5[1]=0;
dGPL2CdL1[1]=(-.632455*L2PL2C[0]*sin(L[1])*cos(L[2])-.4743422525*L2PL2C[0]*cos(L[1])*cos(L[2])-
.22360446525*L2PL2C[0]*cos(L[1])*sin(L[2])+.1677037033714*L2PL2C[0]*sin(L[1])*sin(L[2])+.632455*
L2PL2C[1]*sin(L[1])*sin(L[2])+.4743422525*L2PL2C[1]*cos(L[1])*sin(L[2])-.22360446525*
L2PL2C[1]*cos(L[1])*cos(L[2])+.167703703371375*L2PL2C[1]*sin(L[1])*cos(L[2])+.59160473155*
L2PL2C[2]*cos(L[1])-.443704486411025*L2PL2C[2]*sin(L[1])-.632455*d12dL1*L2PL2C[0]*cos(L[1])*
sin(L[2])+.4743422525*dL2dL1*L2PL2C[0]*sin(L[1])*sin(L[2])-.22360446525*d12dL1*L2PL2C[0]*
sin(L[1])*cos(L[2])-.167703703371375*dL2dL1*L2PL2C[0]*cos(L[1])*cos(L[2])-.57281908427905*
dL2dL1*L2PL2C[0]*cos(L[2])-.632455*dL2dL1*L2PL2C[1]*cos(L[1])*cos(L[2])+.4743422525*
dL2dL1*L2PL2C[1]*cos(L[1])*sin(L[2])+.22360446525*dL2dL1*L2PL2C[1]*sin(L[1])*sin(L[2])+
.167703703371375*dL2dL1*L2PL2C[1]*cos(L[1])*sin(L[2])+.57281908427905*dL2dL1*L2PL2C[1]*sin(L[2]));
dGPL2CdL5[1]=dL2dL5*(-.632455*L2PL2C[0]*cos(L[1])*sin(L[2])+.4743422525*L2PL2C[0]*sin(L[1])*sin(L[2])-
.22360446525*L2PL2C[0]*sin(L[1])*cos(L[2])-.167703703371375*L2PL2C[0]*cos(L[1])*cos(L[2])-
.57281908427905*L2PL2C[0]*cos(L[2])-
.632455*L2PL2C[1]*cos(L[1])*cos(L[2])+.4743422525*L2PL2C[1]*sin(L[1])*cos(L[2])+.22360446525*
L2PL2C[1]*sin(L[1])*sin(L[2])+.167703703371375*L2PL2C[1]*cos(L[1])*sin(L[2])+.57281908427905*
L2PL2C[1]*sin(L[2]));
dGPL4CdL1[1]=0;
dGPL4CdL5[1]=(-.632455*sin(L[5])*L4PL4C[0]-.47434*cos(L[5])*L4PL4C[0]+.22360446525*L4PL4C[1]*cos(L[5])-
.167702907*L4PL4C[1]*sin(L[5])+.59160473155*L4PL4C[2]*cos(L[5])-.4437023794*L4PL4C[2]*sin(L[5]));
dGPL3CdL1[1 ]=dL4dL1*(-.632455*L3PL3C[0]*sin(L[4])*cos(L[5])+.47434*L3PL3C[0]*sin(L[5])*sin(L[4])-
.22360446525*L3PL3C[0]*sin(L[5])*cos(L[4])-.167702907*L3PL3C[0]*cos(L[4])*cos(L[5])-
*.5728170217*L3PL3C[0]*cos(L[4])+.44721525505*L3PL3C[1]*cos(L[4])*cos(L[5])-
.3354105574*L3PL3C[1]*sin(L[5])*cos(L[4])-.1581129534229275*L3PL3C[1]*sin(L[5])*sin(L[4])-
.11858440256877*L3PL3C[1]*sin(L[4])*cos(L[5])-
.405044644214287*L3PL3C[1]*sin(L[4])+.44721525505*L3PL3C[2]*cos(L[4])*cos(L[5])-
.3354105574*L3PL3C[2]*sin(L[5])*cos(L[4])-.1581129534229275*L3PL3C[2]*sin(L[5])*sin(L[4])-
.11858440256677*L3PL3C[2]*sin(L[4])*cos(L[5])-.705044644214287*L3PL3C[2]*sin(L[4]));
dGPL3CdL5[1]=-(.22360446525*L3PL3C[0]*sin(L[4])*cos(L[5])+.3354105574*L3PL3C[2]*sin(L[4])*cos(L[5])+
.11858440256877*L3PL3C[1]*sin(L[5])*cos(L[4])+.3354105574*L3PL3C[1]*sin(L[4])*cos(L[5])-
.167702907*L3PL3C[0]*sin(L[5])*sin(L[4])+.47434*L3PL3C[0]*cos(L[4])*cos(L[5])+.118584402569
*L3PL3C[2]*sin(L[5])*cos(L[4])+.4183296217263205*L3PL3C[1]*cos(L[5])-
.1581129534229275*L3PL3C[2]*cos(L[4])*cos(L[5])+.44721525505*L3PL3C[2]*sin(L[5])*sin(L[4])+
.44721525505*L3PL3C[1]*sin(L[5])*sin(L[4])-.1581129534229275*L3PL3C[1]*cos(L[4])*cos(L[5])+
.313746389497534*L3PL3C[2]*sin(L[5])-.313746389497534*L3PL3C[1]*sin(L[5])+.632455*
L3PL3C[0]*sin(L[5])*cos(L[4])+.705044644214287*dL4dL5*L3PL3C[2]*sin(L[4])+.705044644214287*
dL4dL5*L3PL3C[1]*sin(L[4])+.572817021 7*dL4dL5*L3PL3C[0]*cos(L[4])+.167702907*dL4dL5*
L3PL3C[0]*cos(L[4])*cos(L[5])+.3354105574*dL4dL5*L3PL3C[1]*sin(L[5])*cos(L[4])+.11858440256877*
dL4dL5*L3PL3C[1]*sin(L[4])*cos(L[5])+.3354105574*dL4dL5*L3PL3C[2]*sin(L[5])*cos(L[4])+
.11858440256877*dL4dL5*L3PL3C[2]*sin(L[4])*cos(L[5])-.4183296217263205.*L3PL3C[2]*cos(L[5])-
.47434*dL4dL5*L3PL3C[0]*sin(L[5])*sin(L[5])*sin(L[4])+.632455*dL4dL5*L3PL3C[0]*sin(L[4])*cos(L[5])+
.22360446525*dL4dL5*L3PL3C[0]*sin(L[5])*cos(L[4])-.44721525505*dL4dL5*L3PL3C[1]*
cos(L[4])*cos(L[5])+.1581129534229275*dL4dL5*L3PL3C[1]*sin(L[5])*sin(L[4])-.44721525505*
dL4dL5*L3PL3C[2]*cos(L[4])*cos(L[5])+.1581129534229275*dL4dL5*L3PL3C[2]*sin(L[5])*sin(L[4]));
// Calculate the gravity compensation torque for each motor
G[1]=-mL1*dGPL1CdL1[1]-mL2*dGPCdL1[1]-mL3*dGPL3CdL1[1]-mL4*dGPL4CdL1[1];
G[2]=-mL1*dGPL1CdL5[1]-mL2*dGPCdL5[1]-mL3*dGPL3CdL5[1]-mL4*dGPL4CdL5[1];
}
```

What is claimed is:

1. An interface mechanism providing motion in at least two degrees of freedom for a user and interfacing said motion with a computer, said interface mechanism comprising:
   a linkage mechanism including a plurality of members pivotably coupled to each other and providing two revolute degrees of freedom about a pivot point located remotely from said plurality of members, said pivot point located at about an intersection of axes of rotation of at least two of said members;
   a user manipulatable object coupled to at least one of said plurality of members, said user manipulatable object being rotatable in said two revolute degrees of freedom about said pivot point; and
   at least one sensor reading said rotation of said user manipulatable object and providing at least one sensor signal indicating a position of said user manipulatable object in said two revolute degrees of freedom, wherein said computer receives an indication of said position.

2. An interface mechanism as recited in claim 1 wherein said plurality of members includes five members coupled in a closed loop such that each of said five members is pivotably coupled to two other members of said five members.

3. An interface mechanism as recited in claim 1 wherein said plurality of members are positioned exclusively on one side of said pivot point, wherein said members are provided within a hemisphere of a sphere defined such that said pivot point is at a center of said sphere and said user manipulatable object can be moved in a workspace that defines at least at portion of a surface of said sphere.

4. An interface mechanism as recited in claim 3 wherein at least a portion of said user manipulatable object extends through said pivot point.

5. An interface mechanism as recited in claim 1 wherein said user manipulatable object is independently translatable with respect to said linkage mechanism along a linear third axis in a third degree of freedom through said pivot point.

6. An interface mechanism as recited in claim 1 wherein said at least one sensor is a plurality of sensors, each of said sensors coupled between two of said members of said linkage mechanism for an associated degree of freedom, said sensors being coupled to said computer system.

7. An interface mechanism as recited in claim 1 further comprising a plurality of actuators, each of said actuators coupled between two of said members of said linkage mechanism for an associated degree of freedom, each of said actuators providing a force on said user manipulatable object in an associated degree of freedom.

8. An interface mechanism as recited in claim 7 further comprising a band drive mechanism coupled between one of said actuators and one of said members, said band drive mechanism transmitting said force generated by said actuator to said user manipulatable object and transmitting movement applied to said user manipulatable object by a user to said sensors.

9. An interface mechanism as recited in claim 8 wherein said band drive mechanism includes a rotating drum rotatably coupled to one of said members and rigidly coupled to another one of said members, said drum being additionally coupled to a spindle by a flat band, wherein said transducer is operative to rotate said spindle and thereby rotate said drum and transmit force to said rigidly-coupled member with substantially no backlash.

10. An interface mechanism for interfacing motion with a computer system, said interface mechanism comprising:
   a plurality of members movable with respect to each other for providing at least one degree of freedom to a user manipulatable object;
   an actuator operative to provide a force in one of said degrees of freedom of said user-manipulable object;
   a sensor operative to provide positions of said user-manipulatable object in said at least one degree of freedom; and
   a band drive mechanism including a capstan and a flat band, said capstan coupled to a particular one of said members and to a rotating shaft of said actuator, wherein said flat band is coupled to said capstan at a first end of said band and coupled to said particular member at a second end of said band, wherein said capstan is coupled to said particular member by said flat band such that force is applied to said particular member in said at least one degree of freedom when said rotating shaft of said actuator is rotated.

11. An interface mechanism as recited in claim 10 wherein said force is applied to said particular member in a linear degree of freedom.

12. An interface mechanism as recited in claim 10 wherein said force is applied to said particular member in a rotary degree of freedom.

13. An interface mechanism as recited in claim 10 wherein said flat band includes two separate bands, wherein each of said bands is coupled to said capstan at first ends and each of said bands is attached to said particular member at a second end.

14. An interface mechanism as recited in claim 12 further comprising a drum rigidly coupled to said particular member and rotatably coupled to another one of said plurality of members, wherein said capstan is coupled to said drum by said flat band.

15. An interface mechanism as recited in claim 14 wherein said particular member is one of five rotatably coupled members provided in a closed loop chain such that each of said members is rotatably coupled to two others of said members.

16. An interface mechanism as recited in claim 15 wherein said plurality of members provide two revolute degrees of freedom to said user manipulatable object about a pivot point located remotely from said plurality of members, said pivot point located at about an intersection of axes of rotation of said members.

17. An interface mechanism as recited in claim 16 wherein said user manipulatable object extends through said pivot point and is movable in said two degrees of freedom.

18. An interface mechanism as recited in claim 17 wherein said user manipulatable object is coupled to a linear axis member, wherein said user manipulatable object and said linear axis member are movable in a third linear degree of freedom.

19. An interface mechanism as recited in claim 18 further comprising a second band drive mechanism including a second capstan and a second flat band, said second capstan coupled to said linear axis member by a flat band and to a rotating shaft of said actuator, such that force is applied to said user manipulatable object in said third linear degree of freedom when said rotating shaft of said actuator is rotated.

20. An interface mechanism as recited in claim 18 wherein said linear axis member is a slide portion of a linear bearing.

21. An interface mechanism as recited in claim 10 wherein said computer system implements a medical simulation and wherein said user-manipulable object is a medical instrument.

22. An interface mechanism as recited in claim 21 wherein said user manipulatable object includes a needle and syringe, and wherein said medical simulation simulates an epidural anesthesia procedure of inserting said needle into tissue, where forces are provided on said needle to realistically simulate said insertion.

23. A method, comprising:
  receiving sensor data from a sensor included on an interface apparatus, the sensor data indicating a position of a manipulatable object in a degree of freedom, the degree of freedom being one of a first rotary degree of freedom, a second rotary degree of freedom and a linear degree of freedom, the interface apparatus including a gimbal, the manipulatable object being movable in the first rotary degree of freedom and the second rotary degree of freedom in a spherical workspace and configured to be rotated about a pivot point spaced apart from the gimbal, the pivot point being located at a center of a sphere defined by the spherical workspace, the manipulatable object further configured to be moved in the linear degree of freedom through said pivot point;
  selecting a physical property profile from a plurality of available physical property profiles based on the position of manipulatable object; and
  outputting a force on the manipulatable object via an actuator included in the interface apparatus, the force output on the manipulatable object being determined, at least in part, from a physical property value of the selected physical property profile.

24. The method of claim 23, wherein the degree of freedom is a linear degree of freedom.

25. The method of claim 23, wherein the selection of the physical property profile from the plurality of available physical property profiles is further dependent on a direction of movement of the manipulatable object along a linear axis.

26. The method of claim 23, wherein said interface apparatus is entirely on one side of a plane intersecting the pivot point such that the manipulatable object is on the other side of the plane from the interface apparatus.

27. The method of claim 23, wherein said interface apparatus includes a closed loop spherical mechanism configured to provide the two rotary degrees of freedom to the manipulatable object about the remote pivot point.

28. The method of claim 23, wherein a computer system coupled to the interface apparatus is configured to execute a medical simulation and display images associated with the medical simulation on a display.

29. A method as recited in claim 28, wherein the medical simulation is a epidural anesthesia simulation, the manipulatable object including a needle having a syringe, and different physical property profiles are selected based on whether the needle is advancing or retracting in a simulated tissue of a simulated patient.

30. The method of claim 28, wherein the determining the position of the manipulatable object includes determining whether the manipulatable object is positioned within a simulated tissue of a simulated patient.

31. The method of claim 30, wherein the physical property profile is selected based on a trajectory of a simulated needle within the simulated tissue.

32. The method of claim 31, wherein the selected physical property profile is operative to output forces simulating the simulated needle encountering a simulated bone.

33. The method of claim 23, further comprising outputting forces from the actuator to compensate for a gravitational force resulting from a weight of at least one of the actuators such that the manipulatable object is configured to be manipulated substantially free from the gravitational force.

34. The method of claim 23, further comprising transmitting the force from the actuator to the manipulatable object using a band drive mechanism including a capstan coupled to the actuator and a flat band configured to couple the to the spherical workspace.

35. An apparatus, comprising:
  a linkage including a plurality of members, the linkage configured to provide at least two rotary degrees of freedom about a pivot point spaced apart from said plurality of members, the pivot point located at an intersection of axes of rotation of at least two members from the plurality of members;
  a manipulandum coupled to at least one member from said plurality of members, said manipulandum being rotatable in said two revolute degrees of freedom about said pivot point; and
  a sensor configured to measure a rotation of the manipuladum and configured to provide at least one sensor signal associcated with a position of the manipulandum in the two revolute degrees of freedom.

36. The apparatus of claim 35, wherein said plurality of members includes five members coupled in a closed loop such that each of said five members is pivotably coupled to two others members of said five members.

37. The apparatus of claim 35, wherein said plurality of members are positioned only on one side of the pivot point, said plurality of members being provided within a hemisphere of a sphere defined such that said point is at a center of the sphere and the manipulandum is configured to be moved in a workspace that defines at least at portion of a surface of said sphere.

38. The apparatus of claim 35, wherein at least a portion of said manipulandum extends through the pivot point.

39. The apparatus of claim 35, wherein said manipulandum is independently translatable with respect to said linkage along a linear third axis in a third degree of freedom through the pivot point.

40. The apparatus of claim 35, wherein said sensor is one from a plurality of sensors, each sensor from said plurality of sensors is coupled between two of said members of said linkage.

41. The apparatus of claim 35, further comprising a plurality of actuators, each actuator from the plurality of said actuators is coupled between two members from the plurality of members of said linkage, each actuator from the plurality of said actuators configured to output a force.

42. The apparatus of claim 41, further comprising a band drive mechanism coupled between one actuator from the plurality of said actuators and one member from the plurality of said members, said band drive mechanism configured to transmit the force to said manipulation and to transmit movement applied to said manipulandum to said sensors.

43. An apparatus, comprising:
  a plurality of members movable with respect to each other for providing at least one degree of freedon to a manipulandum;
  an actuator having a rotating shaft and configured to provide a force in one of the at leaset one degree of freedom of said manipulandum;
  a sensor configured to provide positions of said manipulandum in said at least one degree of freedon; and
  a band drive mechanism including a capstan and a flat band, said capstan being coupled to a first member from said plurality of members and to the rotating shaft of said actuator, said flat band being coupled to said capstan at a first end of said flat band and coupled to the first member at a second end of said flat band, said capstan being coupled to the first member by said flat band such that force is applied to the first member in the at least one degree of freedom when said rotating shaft of said actuator is rotated.

* * * * *